United States Patent

Ohashi

[11] Patent Number: 5,949,890
[45] Date of Patent: Sep. 7, 1999

[54] ACTIVE NOISE CONTROL APPARATUS AND WAVEFORM TRANSFORMING APPARATUS THROUGH NEURAL NETWORK

[75] Inventor: Tadashi Ohashi, Kawasaki, Japan

[73] Assignee: Fujitsu Limited, Kawasaki, Japan

[21] Appl. No.: 08/758,260

[22] Filed: Nov. 27, 1996

[30] Foreign Application Priority Data

Nov. 30, 1995 [JP] Japan .................................. 7-312173

[51] Int. Cl.⁶ .................................................. H03B 29/00
[52] U.S. Cl. ........................................................ 381/71.11
[58] Field of Search ........................... 381/71.8, 71.11, 381/71.12, 86; 364/528.15

[56] References Cited

U.S. PATENT DOCUMENTS

| | | |
|---|---|---|
| 4,665,549 | 5/1987 | Eriksson et al. . |
| 4,677,676 | 6/1987 | Eriksson . |
| 4,677,677 | 6/1987 | Eriksson . |
| 4,815,139 | 3/1989 | Eriksson et al. . |
| 4,947,356 | 8/1990 | Elliott et al. . |
| 4,987,598 | 1/1991 | Eriksson . |
| 5,033,082 | 7/1991 | Eriksson et al. . |
| 5,170,433 | 12/1992 | Elliott et al. . |
| 5,313,407 | 5/1994 | Tiernan et al. .......................... 364/508 |
| 5,386,689 | 2/1995 | Bozich et al. ........................... 415/119 |
| 5,434,783 | 7/1995 | Pal et al. .................................. 364/508 |

OTHER PUBLICATIONS

Japanese Abstract No. 4–355797 (Dec. 9, 1992).

*Primary Examiner*—Vivian Chang
*Attorney, Agent, or Firm*—Staas & Halsey

[57] ABSTRACT

Noise data from a noise source is provided for a neural network. An output signal from the neural network is provided for a node of a hidden layer H of the neural network. The weight of the neural network is updated by an update unit according to an error signal $e_{j0}$ detected by a microphone, thereby outputting a deadening sound from a speaker.

17 Claims, 17 Drawing Sheets

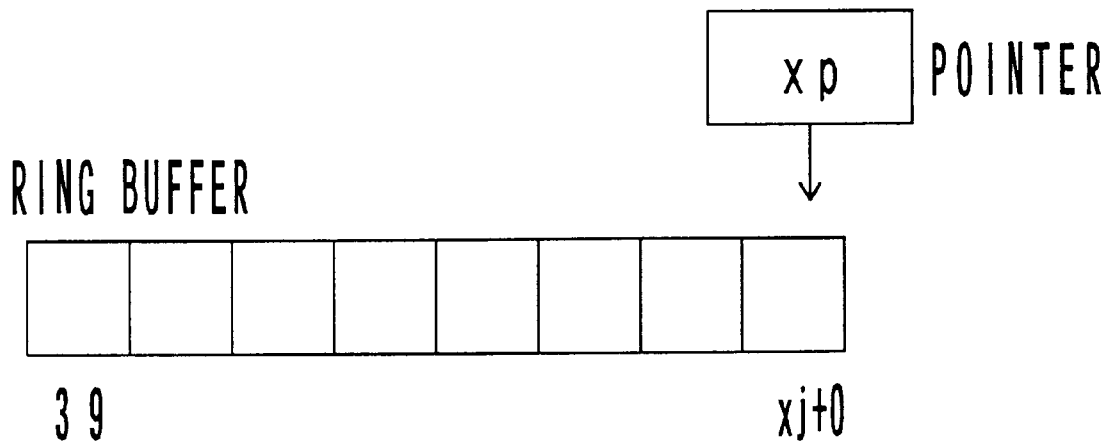
F I G. 1 1 A
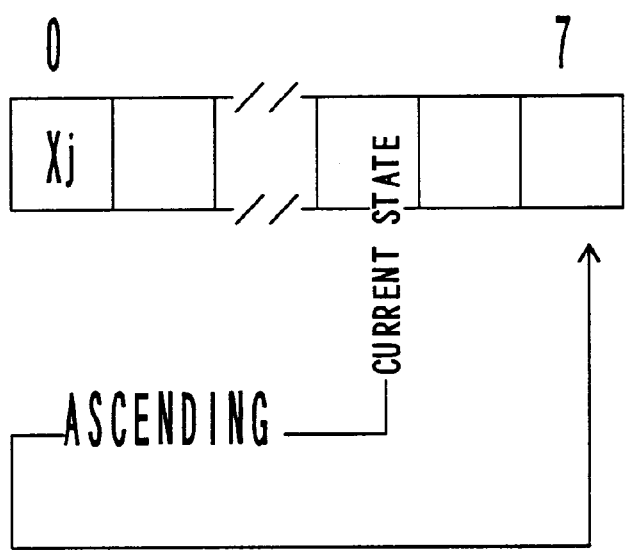
F I G. 1 1 B

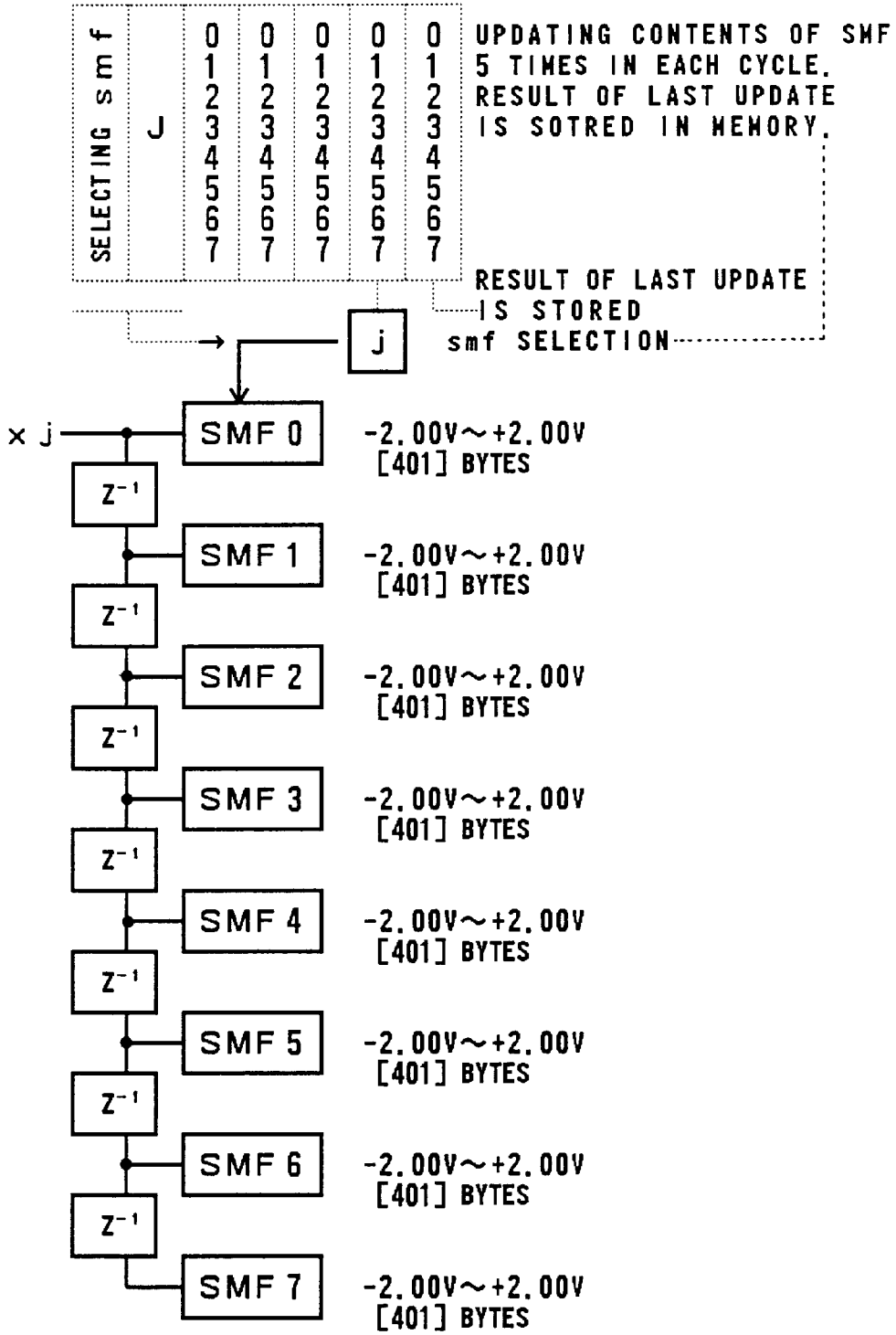
F I G. 1 2

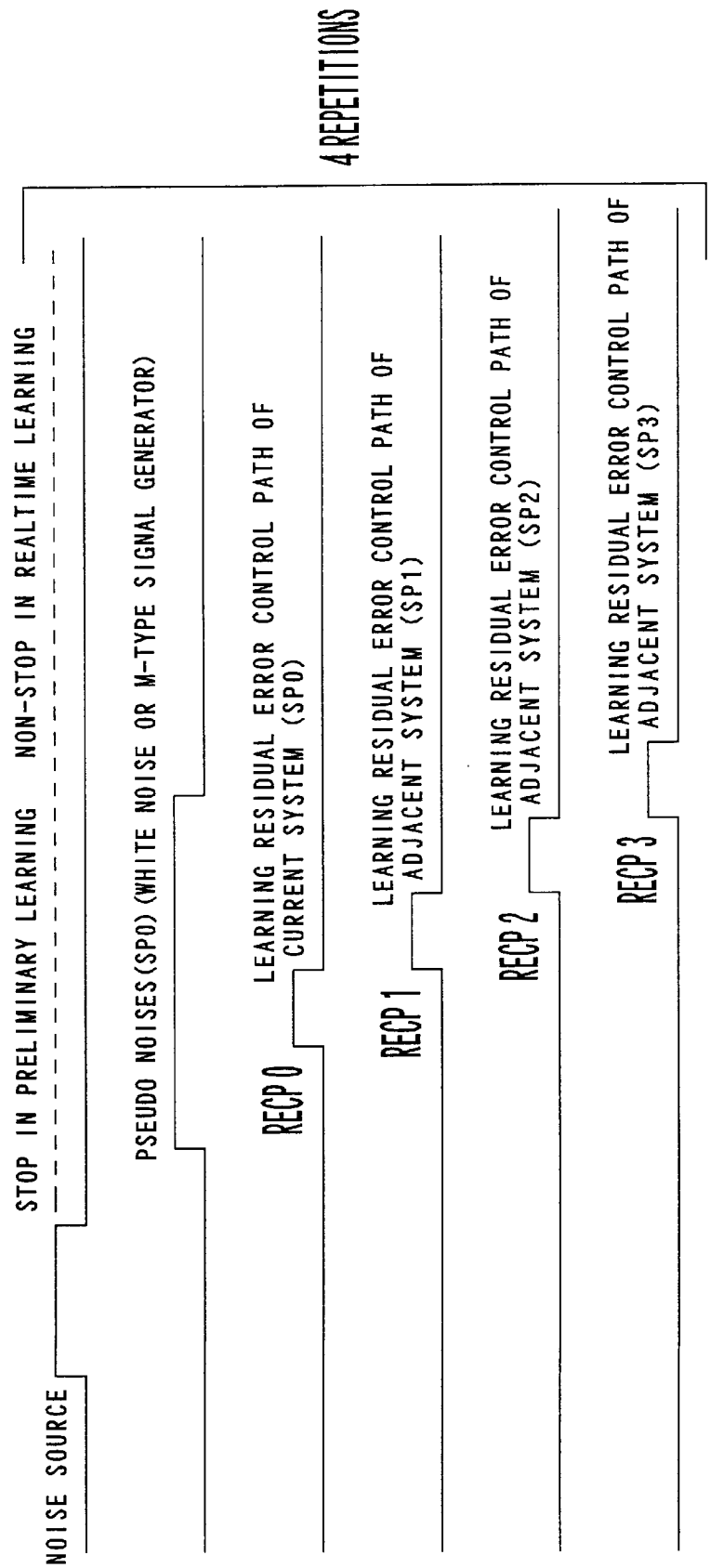
F I G. 15

ACTIVE NOISE CONTROL APPARATUS AND WAVEFORM TRANSFORMING APPARATUS THROUGH NEURAL NETWORK

BACKGROUND OF THE INVENTION

1. Field of the Invention

The present invention relates to an active noise control apparatus and a waveform transforming apparatus, and is effectively used in actively attenuating noises by outputting cancelling sounds from a speaker against the noises to combine the cancelling sounds and the noises.

2. Description of the Related Art

A conventional noise attenuating method is to attenuate noises by actively combining, in amplitude, generated sounds against the noises. For example, noises can be cancelling by generating sounds opposite in amplitude to the noises through an FIR filter, radiating the sounds from a speaker, and combining the noises with the sounds opposite to the noises in amplitude.

FIG. 1 is a block diagram showing the configuration of such a conventional active noise control apparatus.

In FIG. 1, a noise control filter 301 comprises an FIR filter. A noise control object system 302 is a system to be noise-controlled. That is, system 302 indicates the transmission characteristics in space from the speaker connected to the noise control filter 301 to a microphone in an acoustic coupling system 303. An update unit 304 updates the filter coefficient of the noise control filter 301. An error pass filter 305 comprises an FIR filter. An operation unit 306 performs an operation using the method of least mean squares.

The filter coefficient of the error pass filter 305 is preliminarily defined according to the impulse response from the noise control object system 302.

For example, an input signal $X_{(n)}$, which is a primary noise generated by, for example, a fan, is input to the noise control filter 301, and the input signal $X_{(n)}$ is filtered through the noise control filter 301 and output as an output signal $Y_{(n)}$. The output signal $Y_{(n)}$ is output through a speaker as a secondary noise to the noise control object system 302 which is, for example, a space coupled to the fan by a duct (not shown) in FIG. 1. The secondary noise output to the noise control object system 302 is transmitted through the noise control object system 302, becomes a cancelling sound $d_{(n)}'$, and combines with the sound $d_{(n)}$ that is the primary noise transmitted through the duct. The composite sound is detected by the microphone, thereby generating an error signal $e_{(n)} = d_{(n)} - d_{(n)}'$.

The error signal $e_{(n)}$ is provided for the update unit 304. The update unit 304 is also provided with an input signal $X_{(n)}$, and an acoustic coupling error signal is generated by passing the input signal $X_{(n)}$ through the error pass filter 305. The update unit 304 refers to a reference signal and determines through the operation unit 306 a filter coefficient of the noise control filter 301 in such a way that the root-mean-square value of the error signal $e_{(n)}$ can be minimized. n refers to a sample number.

However, assuming that the frequency of the sound to be cancelled ranges from 20 Hz to 1 kHz, the impulse response is 20 mS, and the time required for a 1-tap process of the FIR filter is 250 μs, the number of taps of the FIR filter is 192 using the conventional active noise control apparatus. If an IIR filter replaces the FIR filter, then the acoustic feedback canceler indicates 224 taps, the adaptive filter indicates 80 taps, and the error pass filter indicates 96 taps. Thus, a total of 400 taps are required. Therefore, a large memory capacity and a long DSP operation time are required to cancel the noises using the cancelling sounds, thereby requiring expensive circuitry and high operation costs.

SUMMARY OF THE INVENTION

An object of the present invention is to provide an active noise control apparatus capable of cancelling noises without requiring a DSP for an FIR filter or an IIR filter.

To solve the above described problem, the present invention includes a first neural network for serially receiving the current and previous time-series data against primary noises, and performing a distributed process on the data in parallel; a second neural network for performing a distributed process in parallel on the current and previous time-series data against primary noises, and for providing output of the second neural network for the first neural network; an error detecting unit for detecting an error signal between the secondary noises generated by the output from the first neural network and the transmitted primary noises; and an update unit for receiving the error signal from the error detecting unit and updating data in such a way that the weights of the first neural network and the second neural network can be updated to cancel the transmitted primary noises. The first neural network outputs cancelling sound data against the input noise data.

That is, a cancelling sound can be generated without a digital filter by producing through the neural network the cancelling sound in a mapping process against the noises from the primary noise source to a speaker and from the speaker to an error detecting microphone, thereby reducing the scale of the circuit. Furthermore, the neural network allows a cancelling sound to be generated against the primary noises even if the noise propagating characteristics of a primary path and an error path are nonlinear.

According to an aspect of the present invention, the secondary noises (cancelling sounds) are output from the speaker, and the error detecting unit is an error detecting microphone.

Also according to an aspect of the present invention, the first neural network generates cancelling sounds for the primary path through which the primary noises are propagated to the speaker, and the second neural network forms an acoustic coupling error system for the error path from the speaker to the error microphone.

According to an aspect of the present invention, the first neural network and the second neural network include a nonlinear function in an input layer, a hidden layer, or an output layer. The update unit updates weight values of the hidden layer, output layer, or both hidden and output layers of the above described first and second neural networks. An output signal from the second neural network is input to the hidden layer or the output layer of the first neural network.

According to an aspect of the present invention, active noise control path, active feedback control path, and residual error control path are learned in real time, and the active feedback control path and residual error control path are preliminarily learned.

An aspect of the present invention comprises a delay unit for delaying the first waveform data; a first neural network for receiving the current and previous first waveform data; a second neural network for receiving the current and previous first waveform data and providing output data for the first neural network; an adding unit for adding the output result from each node in the output layer of the first neural network and outputting the second waveform data; an error detecting unit for detecting an error between the waveform corresponding to the first waveform data and the waveform corresponding to the second waveform data; and an update unit for updating based on the difference the weight values and nonlinear functions of the first and second neural networks. The weight values and nonlinear functions of the first and second neural networks are updated in such a way that the waveform corresponding to the first waveform data can be converted into a desired wave form corresponding to the second waveform data.

BRIEF DESCRIPTION OF THE DRAWINGS

FIGS. 11A and 11B show configurations of the ring buffer according to an embodiment of the present invention;

FIG. 12 shows the method of updating the nonlinear function of the active noise control apparatus according to an embodiment of the present invention;

FIG. 15 is a timing chart for the learning process of the residual error control path according to an embodiment of the present invention.

DETAILED DESCRIPTION OF THE PREFERRED EMBODIMENT

An active noise control apparatus according to the first embodiment of the present invention is described below with reference to the attached drawings.

Figure 2:
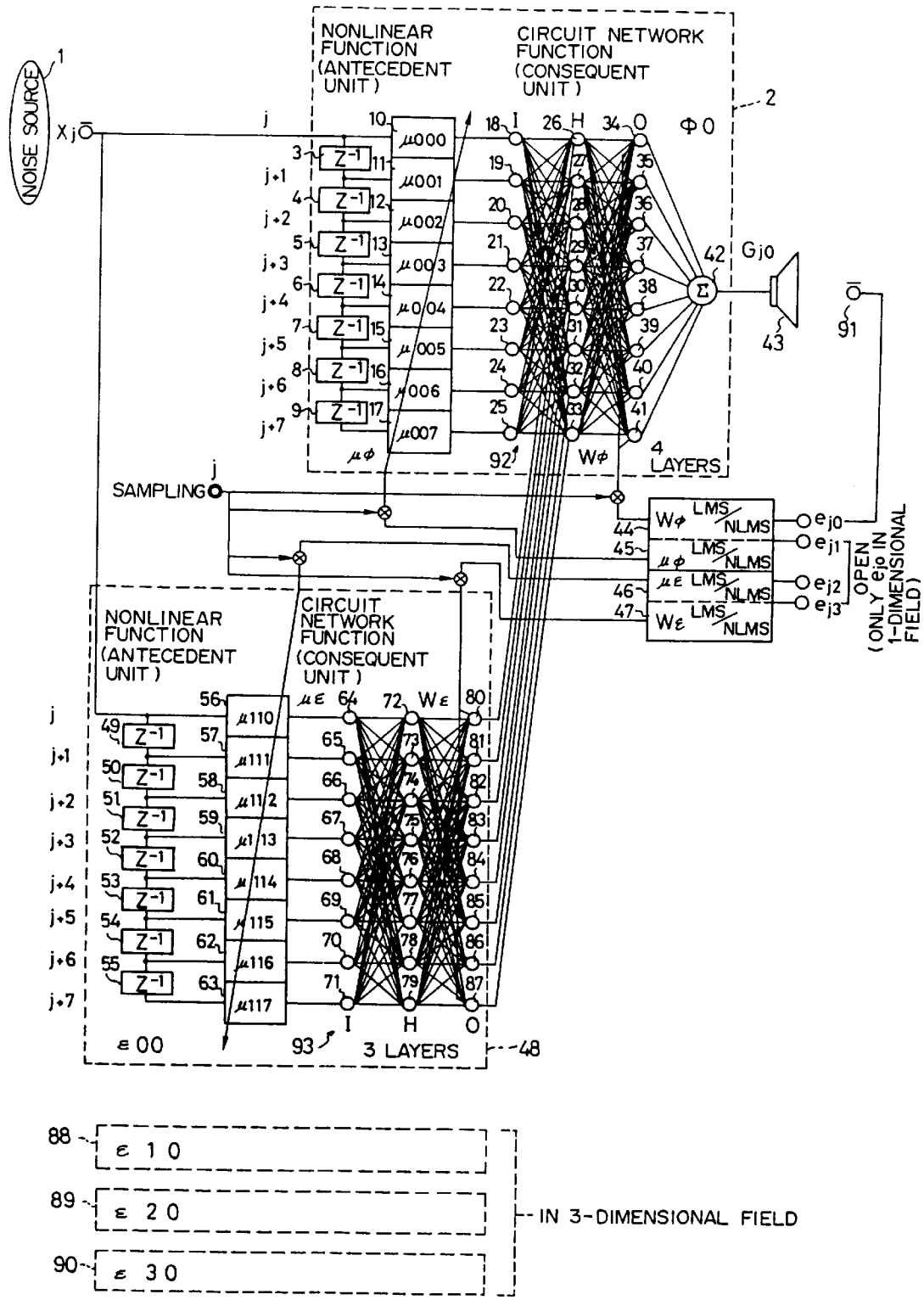
FIG. 2 is a block diagram showing the configuration of the active noise control apparatus according to the first embodiment of the present invention.

FIG. 2 is a block diagram showing a configuration of the active noise control apparatus according to the first embodiment of the present invention.

In FIG. 2, a noise source 1 generates a primary noise. 2 is a noise control unit. 48 and 88 through 90 are acoustic coupling error processing units. 3 through 9 and 49 through 55 are delay elements. 10 through 17 and 56 through 63 are nonlinear functions. 92 and 93 are neural networks. 18 through 25 are nodes in the input layer I in the neural network 92. 26 through 33 are nodes in the hidden layer H in the neural network 92. 34 through 41 are nodes in the output layer O in the neural network 92. 64 through 71 are nodes in the input layer I in the neural network 93. 72 through 79 are nodes in the hidden layer H in the neural network 93. 80 through 87 are nodes in the output layer O in the neural network 93. 42 is an adder. A speaker 43 generates secondary noises. 91 is a microphone. An update unit 44 updates the weight of the output layer O in the neural network 92. 45 is an update unit for the nonlinear functions 10 through 17. 46 is a update unit for the nonlinear functions 56 through 63. An update unit 47 updates the weight of the output layer O in the neural network 93. The neural network 92, forming part of the noise control unit 2, generates a cancelling sound for the primary path from the primary noises source 1 to the speaker 43. The neural network 93, forming part of the acoustic coupling error processing unit 48, forms an acoustic coupling error system for an error path from the speaker 43 to the microphone 91.

Described below are the operations of the active noise control apparatus according to the first embodiment of the present invention.

Figure 1:
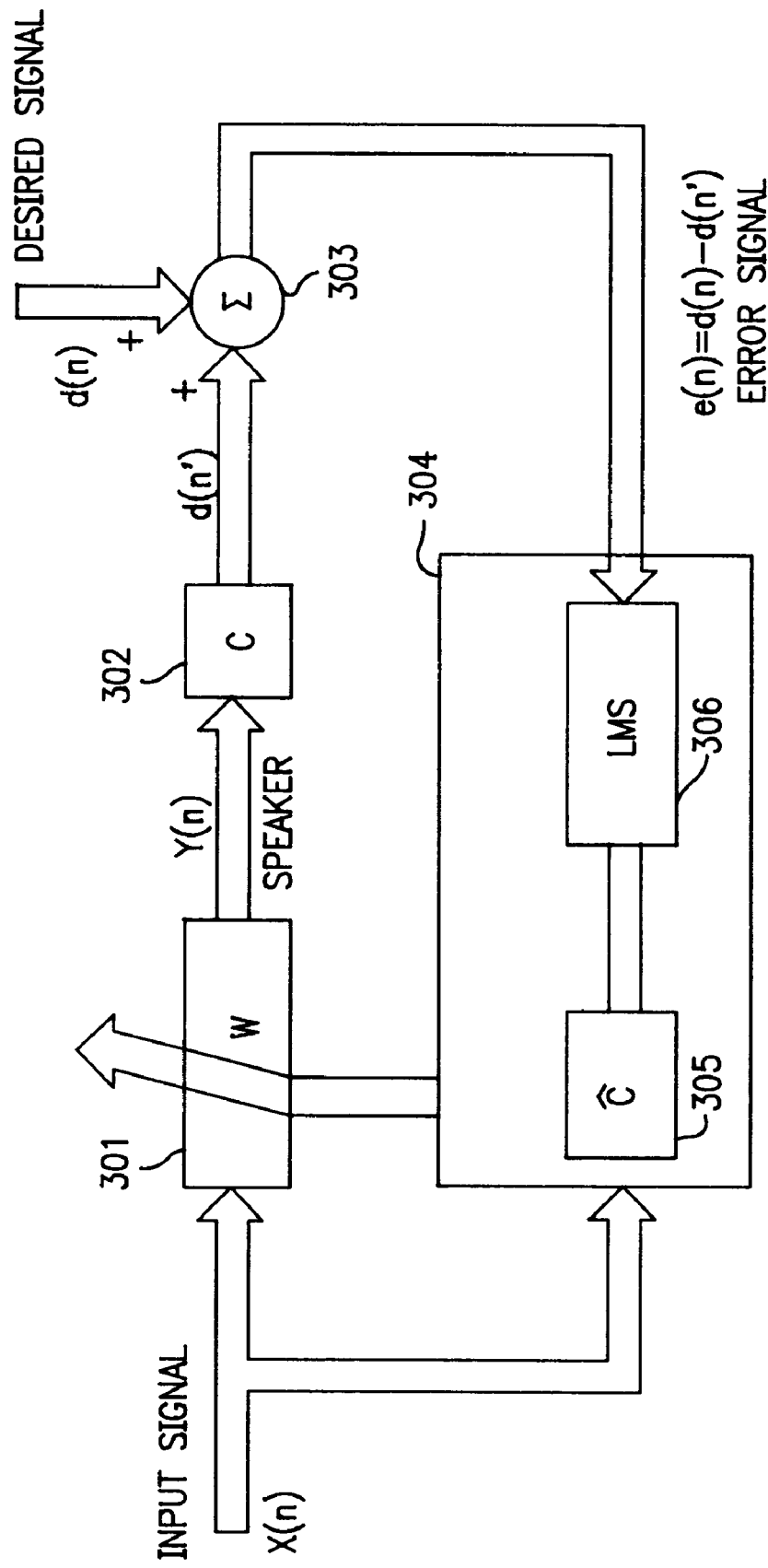
FIG. 1 is a block diagram showing the configuration of the conventional active noise control apparatus.

For example, an input signal Xj corresponding to the primary noises from the noise source 1, which comprises, for example, an air fan provided in an electronic appliance as shown in FIG. 1, is provided for the neural network 92 forming part of the noise control unit 2. Input signal Xj is delayed in unit time by the delay elements 3 through 9. The current input signal Xj, and the previous input signals Xj delayed by the delay elements 3 through 9, are provided for the nonlinear functions 10 through 17 respectively.

The nonlinear functions 10 through 17 perform a function process on the current input signal Xj and the previous input signals Xj delayed by the delay elements 3 through 9. Nonlinear functions 10 through 17 provide the process results for the nodes 18 through 25 in the input layer I in the neural network 92.

An input signal provided for the nodes 18 through 25 in the input layer I in the neural network 92 is assigned a corresponding weight value determined between the nodes 18 through 25 in the input layer I and the nodes 26 through 33 in the hidden layer H. The results are provided for each of the nodes 26 through 33 in the hidden layer H of the neural network 92.

Each of the nodes 26 through 33 in the hidden layer H in the neural network 92 generates an output signal to another neuron. The generated output signal is based on an input signal provided from each of the nodes 18 through 25 in the input layer I and an input signal provided from each of the nodes 80 through 87 in the output layer O in the neural network 93 forming part of the acoustic coupling error processing unit 48.

An output signal from each of the nodes 26 through 33 in the hidden layer H is assigned a corresponding weight value determined between the nodes 26 through 33 in the hidden layer H and the nodes 34 through 41 in the output layer O. The results are provided for each of the nodes 34 through 41 in the output layer O of the neural network 92.

Each of the nodes 34 through 41 in the output layer O in the neural network 92 generates an output signal to an adder 42. The generated output signal is based on an input signal provided by each of the nodes 26 through 33 in the hidden layer H.

The adder 42 adds the output signal from each of the nodes 34 through 41 in the output layer O and provides the sum to the speaker 43.

The secondary noises are output from the speaker 43 to the space using the fan. The primary noises transmitted and the secondary noises output through the speaker 43 are detected by the microphone 91 through the acoustic coupling system. The microphone 91 provides an error signal $e_{j0}$ corresponding to the error between the transmitted primary noises and secondary noises for the update units 44 through 47. Therefore, the microphone 91 functions as error detecting unit.

The neural network 92 obtains secondary noises (cancelling sounds) in a mapping process to cancel the primary noises transmitted through the primary path from the noise source to the speaker.

The input signal Xj corresponding to the primary noises from the noise source 1 is also provided for the neural network 93 forming part of the acoustic coupling error processing unit 48 and is delayed in unit time by the delay elements 49 through 55. The current input signal Xj and the previous input signal Xj delayed by the delay elements 49 through 55 are provided for the nonlinear functions 56 through 63 respectively.

The nonlinear functions 56 through 63 perform function processes on the current input signal Xj and the previous input signal Xj delayed by the delay elements 49 through 55, and provide the process results for the nodes 64 through 71 respectively in the input layer I in the neural network 93.

The input signal provided for the nodes 64 through 71 in the input layer I in the neural network 93 is assigned a corresponding weight value determined between the nodes 64 through 71 in the input layer I and the nodes 72 through 79 in the hidden layer H, and then provided for each of the nodes 72 through 79 in the hidden layer H in the neural network 93.

The nodes 72 through 79 in the hidden layer H in the neural network 93 generate an output signal to another neuron based on the input signal provided from each of the nodes 64 through 71 in the input layer I.

The output signal from each of the nodes 72 through 79 in the hidden layer H is assigned a corresponding weight value determined between each of the nodes 72 through 79 in the hidden layer H and each of the nodes 80 through 87 in the output layer O, and is then provided for each of the nodes 80 through 87 in the output layer O in the neural network 93.

Each of the nodes 80 through 87 in the output layer O in the neural network 93 generates an output signal for each of the nodes 72 through 79 in the hidden layer H in the neural network 92 based on the input signal provided from each of the nodes 72 through 79 in the hidden layer H.

The neural network 93 forms an acoustic coupling error system for the error path from the speaker 43 to the error microphone 91.

The update unit 44 updates a weight value in each of the nodes 34 through 41 in the output layer O in the neural network 92 based on an error signal $e_{j0}$ by the LMS method (method of least mean squares) or the NLMS method (normalized LMS method) on the sampling cycle.

The update unit 45 updates the nonlinear functions 10 through 17 based on an error signal $e_{j0}$ by the LMS method (method of least mean squares) or the NLMS method (normalized LMS method) on the sampling cycle.

The update unit 46 updates the nonlinear functions 56 through 63 based on an error signal $e_{j0}$ by the LMS method (method of least mean squares) or the NLMS method (normalized LMS method) on the sampling cycle.

The update unit 47 updates the weight value in each of the nodes 80 through 87 in the output layer O in the neural network 93 based on an error signal $e_{j0}$ by the LMS method (method of least mean squares) or the NLMS method (normalized LMS method) on the sampling cycle.

That is, the primary noises generated by the noise source 1 of a fan reach the microphone 91 through the primary path of a duct. The weight of neural network 92 and nonlinear function is updated in a way that the primary noises transmitted from the noise source 1 to the speaker 43 which generates the secondary noises can be successfully cancelled. The weight of neural network 93 and nonlinear function is updated in such a way that the primary noises transmitted through an error path from the speaker 43 to the microphone 91 can be successfully cancelled. Therefore, the neural network 93 operates such that a coupling process can be performed with the items of the coupling $\tilde{C}$ exchanged.

When the update units 44, 45, 46, and 47 update data by the LMS method or the NLMS method, the error signal $e_{j0}$ is minimized or ideally zero. That is, the primary noises are cancelled by the secondary noises to prevent the noises generated by the fan from being detected in the microphone 91.

In the case of a one-dimensional sound field, the input terminal of error signals $e_{j1}$, $e_{j2}$, and $e_{j3}$ is set open.

The method of updating the weight of the neural networks 92 and 93 through the update units 44 through 47 can be the method of least mean squares (LMS method) in which the weight is determined such that a root-mean-square value of an error signal $e_{j0}$ can be minimized, the normalized least mean square method (NLMS method), filtered X algorithm, multiple control algorithm, etc. in addition to the method of updating a weight value by adding an error signal $e_{j0}$ of a constant ratio to the current weight value.

Acoustic coupling error process units 88 through 90 for use in a 3-dimensional sound field have the same configuration as the acoustic coupling error processing unit 48.

Figure 3:
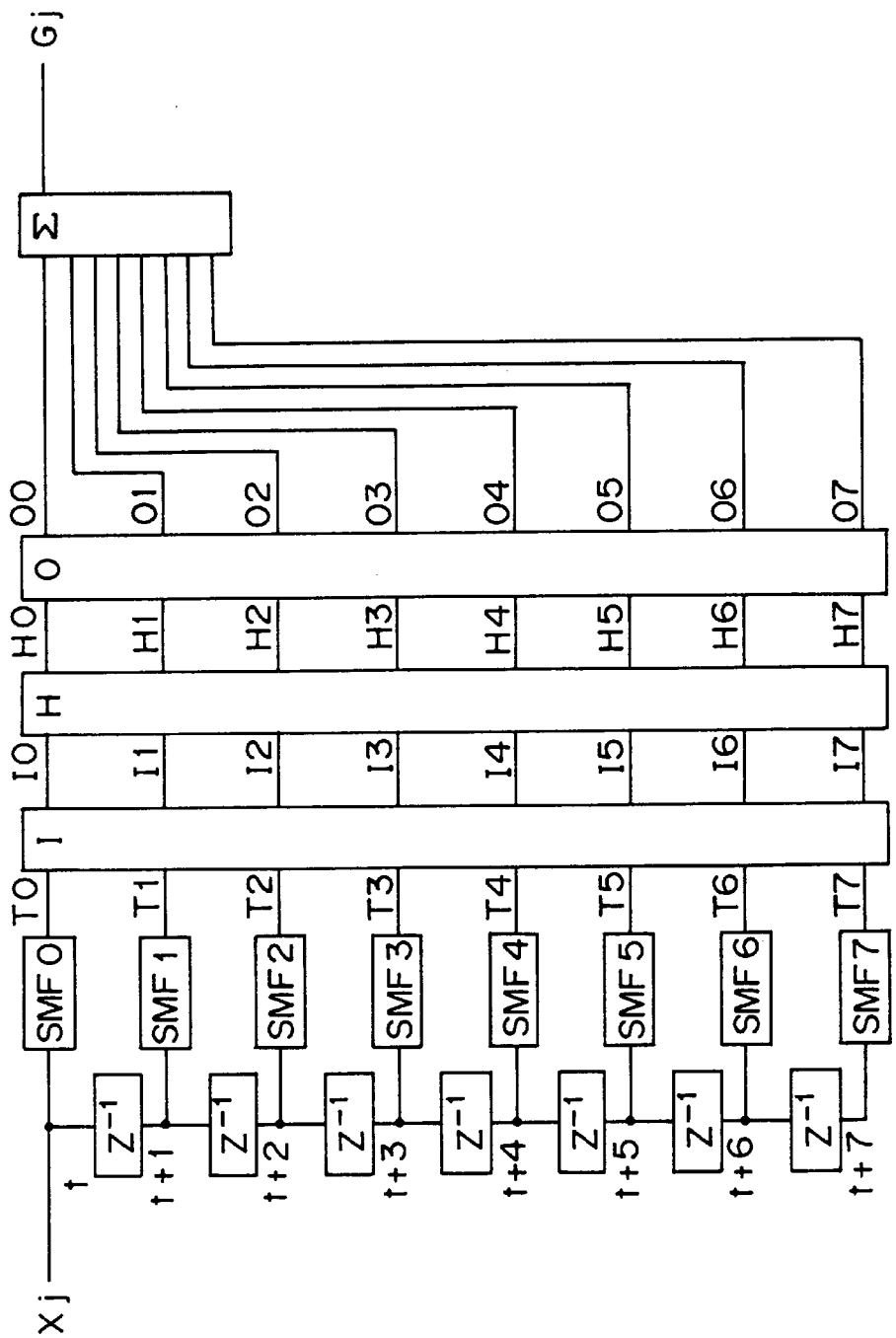
FIG. 3 is a block diagram showing the outline of the configuration of the active noise control apparatus according to the first embodiment of the present invention.

FIG. 3 is a block diagram simply showing the configuration of the noise control unit 2 shown in FIG. 2.

In FIG. 3, an input signal Xj is delayed by a delay element $Z^{-1}$, an input signal Xj at time t is input to a nonlinear function SMF0, an input signal Xj at time t+1 is input to a nonlinear function SMF1, an input signal Xj at time t+2 is input to a nonlinear function SMF2, an input signal Xj at time t+3 is input to a nonlinear function SMF3, an input signal Xj at time t+4 is input to a nonlinear function SMF4, an input signal Xj at time t+5 is input to a nonlinear function SMF5, an input signal Xj at time t+6 is input to a nonlinear function SMF6, and an input signal Xj at time t+7 is input to a nonlinear function SMF7, Output signals T0 through T7 from the nonlinear functions SMF0 through SMF7 are input to the layer I. Output signals I0 through I7 from the layer I are assigned respective weight values and input to the layer H. Output signals H0 through H7 from the layer H are assigned respective weight values and input to the layer O. Output signals O0 through O7 from the layer O are added by the adder $\Sigma$, and an output signal Gj is generated.

FIG. 4 is a time chart showing the operations of the active noise control apparatus according to the first embodiment of the present invention.

Figure 4A:
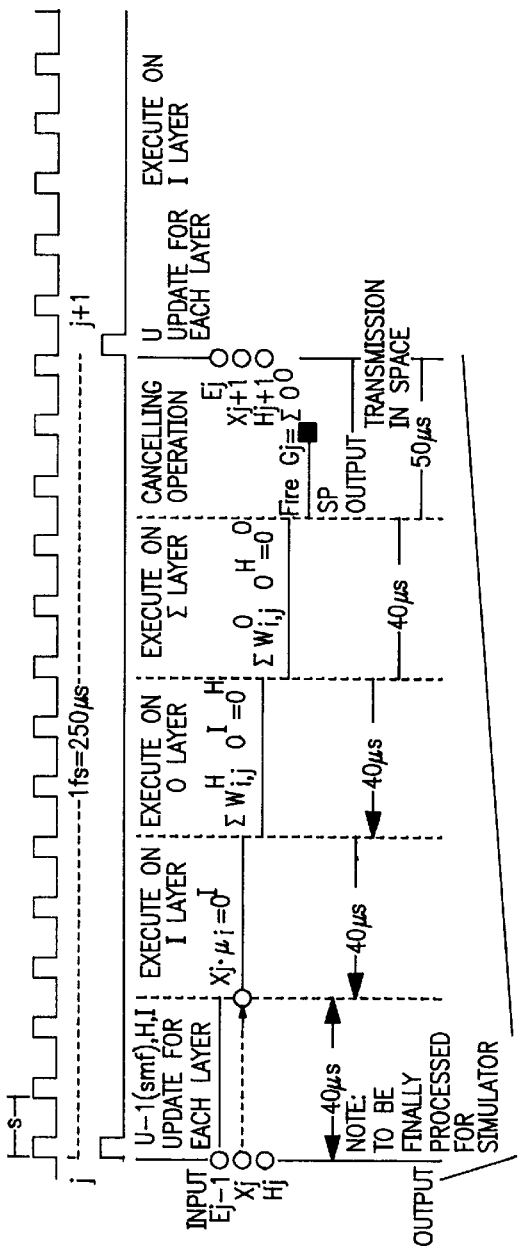
FIGS. 4A and 4B are time charts showing the operations of the active noise control apparatus according to an embodiment of the present invention.

As shown in FIG. 4A, for example, 1fs (sampling frequency) equals 250 $\mu$s. In 1fs, the nonlinear functions SMF0 through SMF7 are updated, the layer H is updated, the layer I is updated, the layer I is executed, the layer O is executed, the layer Σ is executed, and a cancelling operation is performed on the j-th input signal Xj and the (j−1)th error signal Ej−1.

The output value $O^I$ of the layer I is calculated as follows.

$$O^I = Xj \cdot \mu_i$$

where $\mu_i$ indicates the grade of the i-th nonlinear functions SMF0 through SMF7.

The output value $O^H$ of the layer H is calculated as follows.

$$O^H = \Sigma W^H_{i,j} O^I$$

where $W^H_{i,j}$ indicates the weight between the i-th layer H and the j-th layer I.

The output value $O^O$ of the layer O is calculated as follows.

$$O^O = \Sigma W^O_{i,j} O^H$$

where $W^O_{i,j}$ indicates the weight between the i-th layer O and the j-th layer H.

The output signal Gj from the adder Σ is represented by:

$$Gj = \Sigma O^O$$

Figure 4B:
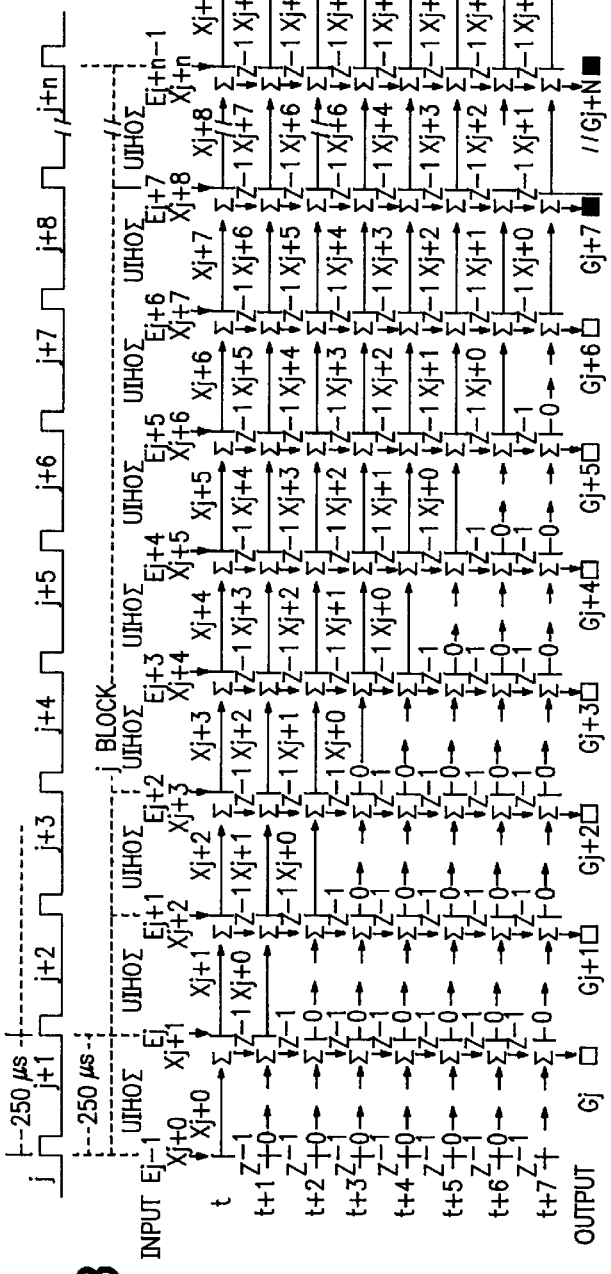

As shown in FIG. 4B, an output signal Gj is generated based on the input signal Xj when the j-th input signal Xj is sampled. An output signal Gj+1 is generated based on the input signals Xj and Xj+1 when the (j+1)th input signal Xj+1 is sampled. An output signal Gj+2 is generated based on the input signals Xj through Xj+2 when the (j+2)th input signal Xj+2 is sampled. An output signal Gj+3 is generated based on the input signals Xj through Xj+3 when the (j+3)th input signal Xj+3 is sampled. An output signal Gj+4 is generated based on the input signals Xj through Xj+4 when the (j+4)th input signal Xj+4 is sampled. An output signal Gj+5 is generated based on the input signals Xj through Xj+5 when the (j+5)th input signal Xj+5 is sampled. An output signal Gj+6 is generated based on the input signals Xj through Xj+6 when the (j+6)th input signal Xj+6 is sampled. An output signal Gj+7 is generated based on the input signals Xj through Xj+7 when the (j+7)th input signal Xj+7 is sampled. An output signal Gj+8 is generated based on the input signals Xj through Xj+8 when the (j+8)th input signal Xj+8 is sampled. An output signal Gj+n is generated based on the input signals Xj+n−7 through Xj+n when the (j+n)th input signal Xj+n is sampled.

Figure 5:
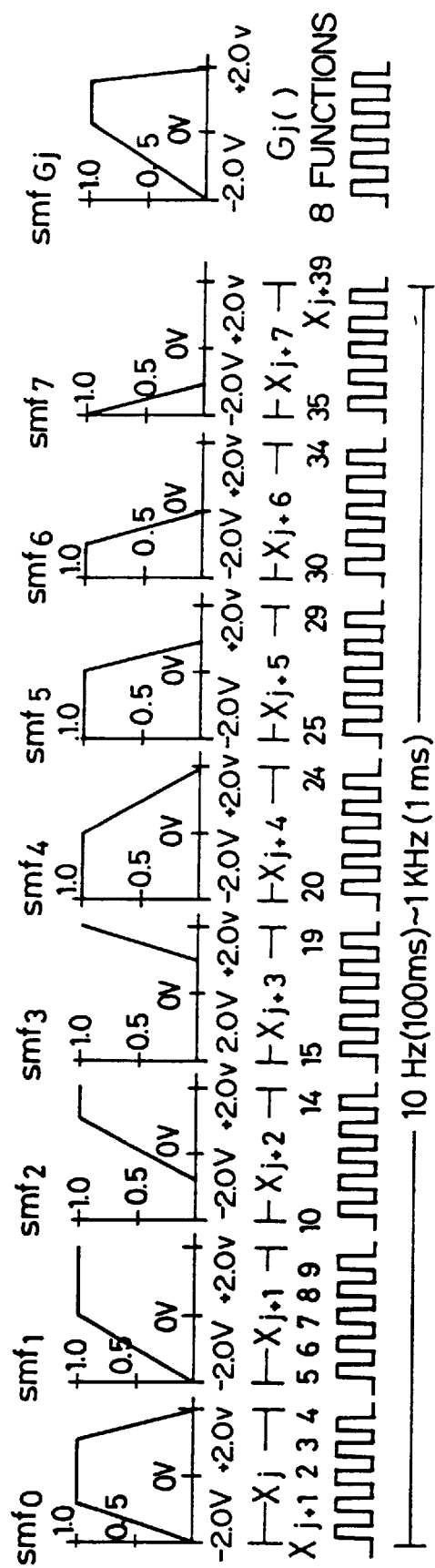
FIG. 5 shows an example of the nonlinear function according to an embodiment of the present invention.

FIG. 5 shows an example of the nonlinear functions SMF0 through SMF7.

In FIG. 5, the nonlinear functions SMF0 through SMF7 can be represented by a series of time spaces of sampling membership functions when the time axis of the sampling frequency of the input signal Xj is set as a horizontal axis.

Figure 6A:
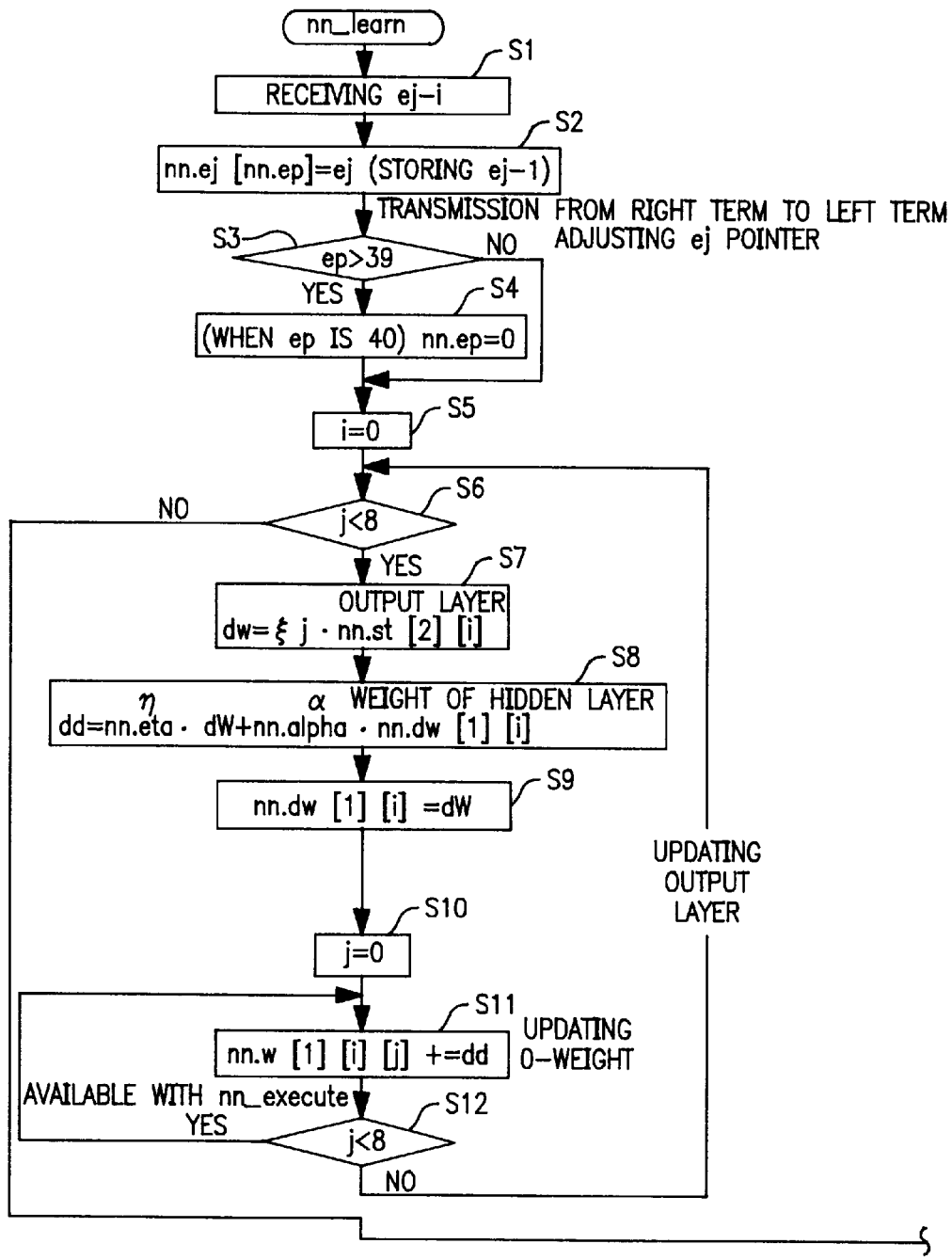
FIG. 6 is a flowchart (1) showing the learning operations of the active noise control apparatus according to an embodiment of the present invention.
Figure 6B:
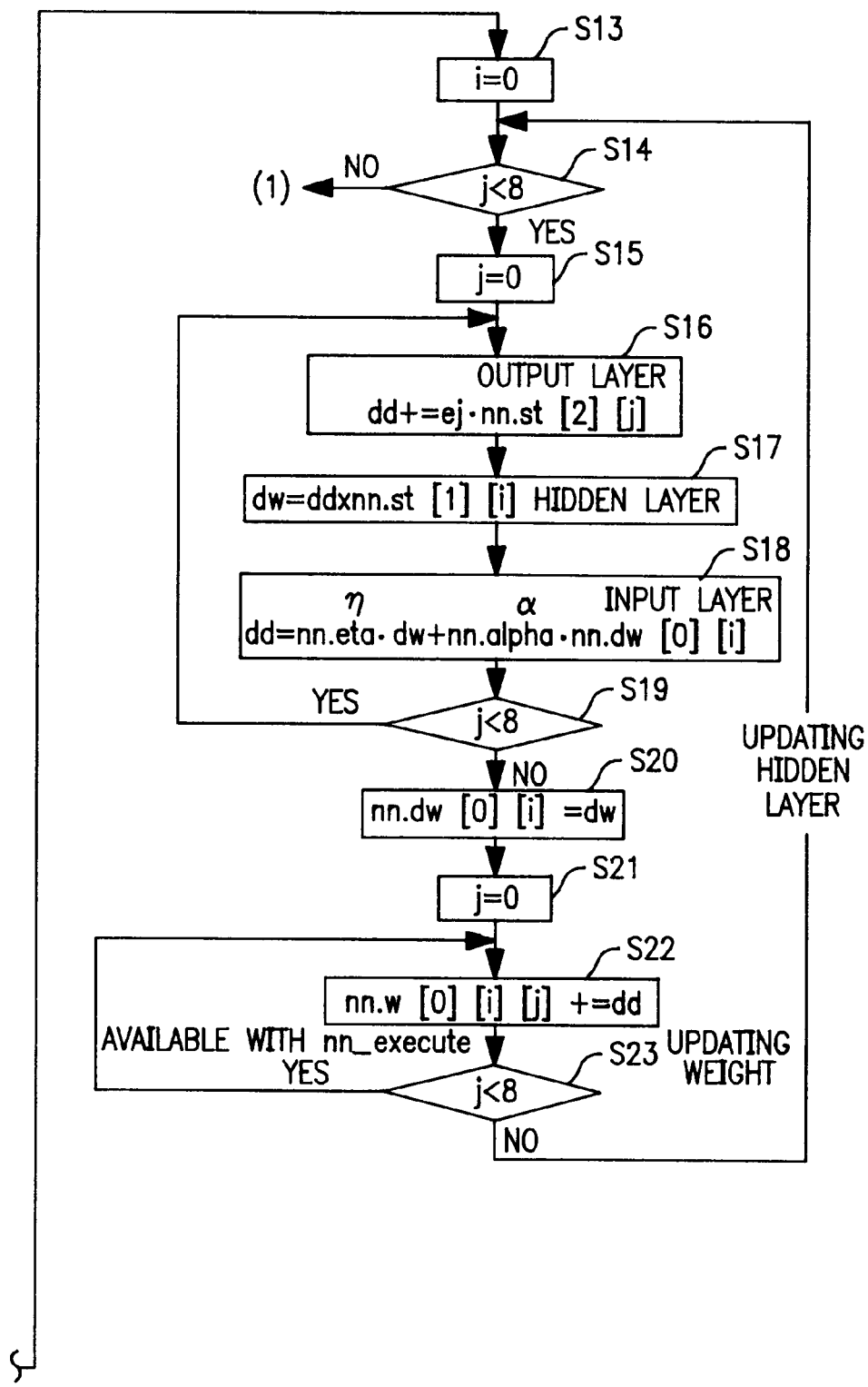
Figure 7A:
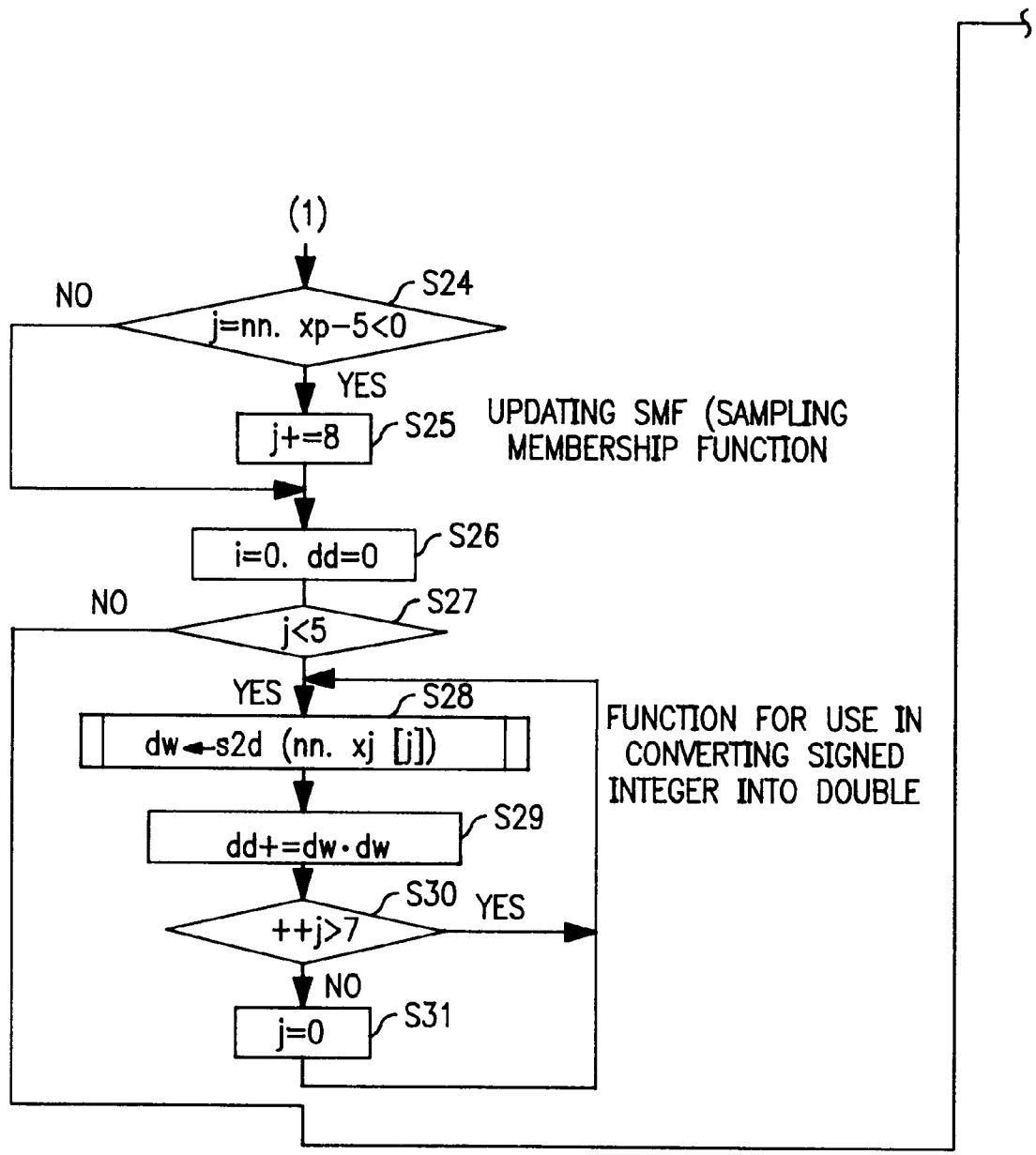
FIG. 7 is a flowchart (2) showing the learning operations of the active noise control apparatus according to an embodiment of the present invention.
Figure 7B:
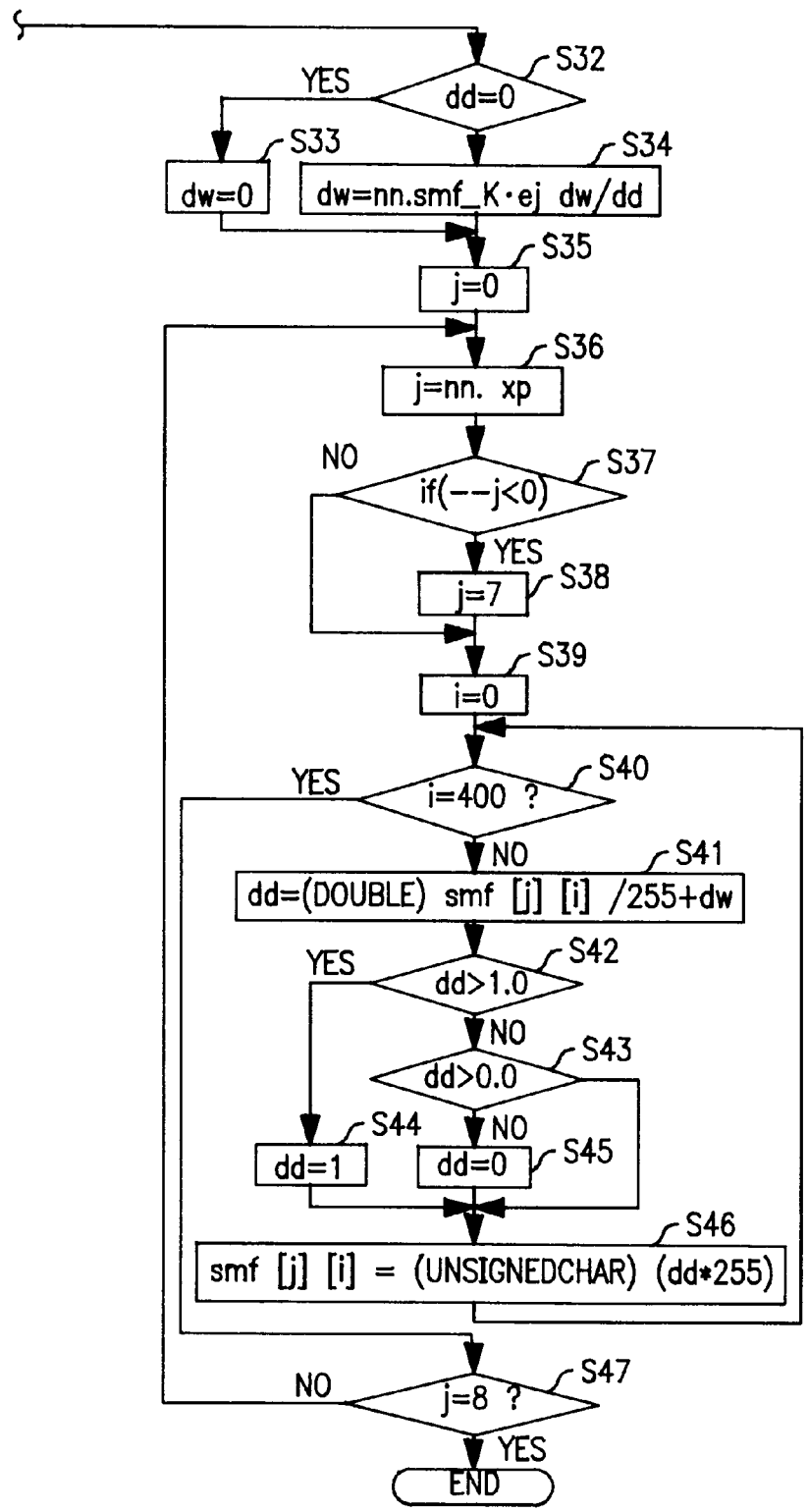

FIGS. 6 and 7 are flowcharts showing the learning operations of the active noise control apparatus according to the first embodiment of the present invention. The flowcharts are prepared using the C language. For example, "&a" indicates the address of the variable a, "a=b" indicates that b is substituted for a, "a+=b" indicates that a+b is substituted for a, "a−=b" indicates that a−b is substituted for a, "a++" or "++a" indicates that 1 is added to a, and "a−−" or "−−a" indicates that 1 is subtracted from a.

The layer O is updated in steps S5 through S12 shown in FIG. 6. The layer H is updated in steps S13 through S23 shown in FIG. 6. Nonlinear functions (sampling membership function) are updated in steps S24 through S47 shown in FIG. 7.

Furthermore, to control noises up to 2 kHz, 40 sampling are set as one cycle.

In FIG. 6, an error signal ej−1 is received in step S1, and is stored in an area pointed to by the value of the error pointer ep in step S2.

Then, it is determined whether or not the value obtained by adding 1 to the value of the error pointer ep is larger than 39 in step S3. If the value of the error pointer ep is 40, then it is set to 0 in step S4 and control is passed to step S5. If the value of the error pointer ep is equal to or smaller than 39, then step S4 is skipped and control is passed to step S5.

Next, 0 is substituted for the variable i in step S5 and it is determined in step S6 whether or not the variable i is smaller than 8. When the variable i is smaller than 8, the layer O is updated in steps S6 through S12. When the variable i is equal to or larger than 8 after the weight values for 8 nodes in the layer O have been updated, control is passed to step S13.

Figure 10A:
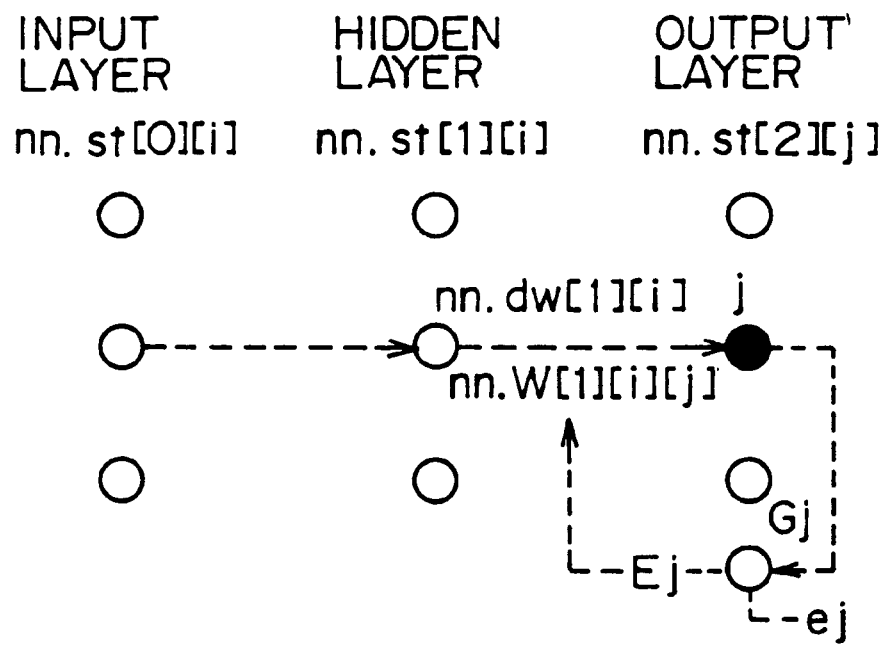
FIGS. 10A and 10B show the method of updating the weight of the active noise control apparatus according to an embodiment of the present invention.

FIG. 10A shows an example of the method of updating the layer O.

In FIG. 10A, nn.st [0][i] indicates a value of the input layer, nn.st [1][i] indicates a value of the hidden layer, and nn.st [2][j] indicates a value of the output layer. Ej is generated based on Gj and ej, and nn.w [1][i][j] is generated based on Ej and nn.dw [1][i].

For example, the update equation of a weight coefficient for the output layer is represented as follows.

$$W(j+1) = W(j) + \eta \Delta W(j) + \alpha \Delta W(j) \qquad (1)$$

where η indicates a learning speed, and
α indicates a learning momentum.
ΔW(j) is represented as follows.

$$\Delta W(j) = (Dj - Gj)(O^O(j))^2 \qquad (2)$$

where Dj indicates an expected value, that is, a value obtained when the input signal Xj reaches the deadening speaker, Gj indicates an output value from the adder Σ, and
$O^O(j)$ indicates an output value from the j-th layer O.

When the layer O is updated in the process shown in FIG. 6, ej·nn. st[2][i] is substituted for dW in step S7, and nn. eta·dW+nn. alpha·nn. dw[1][i] for dd in step S8. The "nn. eta" indicates Learning Speed η, and "nn. alpha" indicates Learning Momentum α.

Next, the weight is computed between the i-th layer O and the j-th layer H in step S11 by substituting dW for nn. dw[1][i] in step S9, substituting 0 for the variable j in step S10, and substituting a sum of dd and nn. w[1][i][j] for nn. w[1][i][j]. If the weight values have been updated between the i-th layer O and 8 nodes in the layer H in step S12 by repeating 8 times the operations in step S11, then control is returned to step S6 and the weight for the next node in the layer O is updated. nn. w[1][i][j] is used in an executable routine.

Then, 0 is substituted for the variable in step S13 and it is determined whether or not the variable i is smaller than 8 (step S14). If the variable i is smaller than 8, then the layer H is updated in steps S15 through S23. When the variable i reaches or exceeds 8 after updating the weight for the 8 nodes in the layer H, control is passed to step S24 as shown in FIG. 7.

Figure 10B:
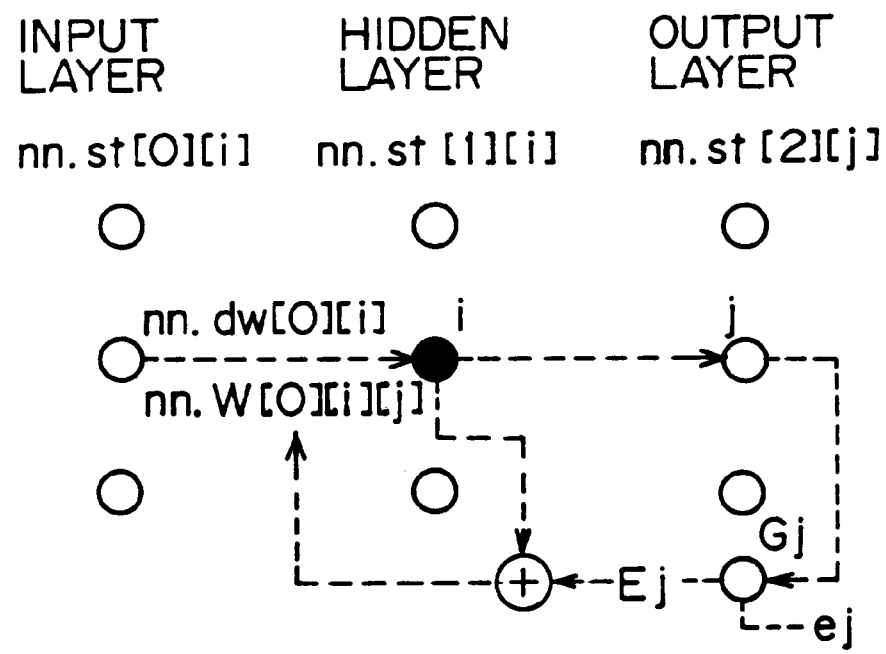

FIG. 10B shows an example of the method of updating the layer H.

In FIG. 10B, nn.st [0][i] indicates a value of the input layer, nn.st [1][i] indicates a value of the hidden layer, and nn.st [2][j] indicates a value of the output layer. Ej is generated based on Gj and ej, and nn.w [0][i][j] is generated based on Ej and nn.dw [0][i].

For example, the update equation of a weight coefficient for the output layer is represented as follows.

$$W(j+1)=W(j)+\eta\Delta W(j)+\alpha\Delta W(j) \quad (3)$$

where η indicates a learning speed, and
α indicates a learning momentum.
ΔW(j) is represented as follows.

$$\Delta W(j)=(Dj-Gj)\,(H^H(j)\,)^2 \quad (4)$$

where Dj indicates an expected value, that is, a value obtained when the input signal Xj reaches the deadening speaker, Gj indicates an output value to the hidden layer, and
$H^H(j)$ indicates an output value of the j-th layer H.

When the layer H is updated as shown in FIG. 6, 0 is substituted for the variable j in step S15, a sum of dd and ej·nn. st[2][j] is substituted for dd in step S16, ddxnn. st[1][i] is substituted for dw in step S17, and nn. eta·dw+nn. alpha·nn. dw[0][i] is substituted for dd in step S18. The "nn. eta" indicates Learning Speed η, and "nn. alpha" indicates Learning Momentum α. It is determined whether or not the variable j is smaller than 8 in step S19. If the variable j is smaller than 8, then control is returned to step S16, the operations in steps S16 through S18 are repeated 8 times, and the weight of the layer H is computed in consideration of the output value from the 8 nodes 80 through 87 in the output layer O of the acoustic coupling error processing unit 48 shown in FIG. 2.

Next, the weight is computed between the i-th layer H and the j-th layer I in step S22 by substituting dW for nn. dw[0][i] in step S20, substituting 0 for the variable j in step S21, and substituting a sum of dd and nn. w[0][i][j]for nn. w[0][i][j]. If the weight values have been updated between the i-th layer H and 8 nodes in the layer I in step S23 by repeating 8 times the operations in step S22, then control is returned to step S14 and the weight for the next node in the layer H is updated. nn. w[0][i][j] is used in an executable routine.

After subtracting 5 from the value of the X pointer nn. xp and substituting the difference for the variable j, it is determined in step S24 whether or not the variable j is smaller than 0. When the variable j is smaller than 0, then a sum of the variable j and 8 is substituted for the variable j in step S25.

FIG. 11A shows a ring buffer storing an input signal Xj. The ring buffer stores an input signal Xj for 40 times of sampling, and the X pointer xp indicates the position of the current input signal Xj.

FIG. 11B shows the operations in step S24, and illustrates that the current value of the ring buffer is reduced by 5 by subtracting 5 from the value of the X pointer nn. xp.

FIG. 12 shows an example of the method of updating the sampling membership function.

Since one cycle includes 40 times of sampling as shown in FIG. 12, the sampling membership function is updated 5 times in one cycle, and only the value of the last sampling is stored in the memory. Furthermore, a 401 BYTES memory is used for sampling membership functions SMF0 through SMF7 with the value of the sampling membership function of, for example, −2V through +2V, and with a resolution of 200 mV.

The update equation of the sampling membership function is, for example, represented as follows.

$$smf(i+1)=smf(i)+K(D(j)-G(j))\,Xj/\Sigma X\,(j-k)^2 \quad (5)$$

where K indicates a step gain of the sampling membership function.

In updating the sampling membership function shown in FIG. 7, 0 is substituted for the variable i, and 0 is substituted for dd in step S26. It is determined in step S27 whether or not the variable i is smaller than 5. If the variable i is smaller than 5, then a signed integer is converted into a "double", the value of xj[j] is substituted for dw in step S28, and a sum of dd and dw·dw is substituted for dd in step S29. It is determined whether or not a sum of the variable j and 1 is larger than 7 in step S30. If the sum is larger than 7, then control is returned to step S28. If the sum is equal to or smaller than 7, then 0 is substituted for the variable j in step S31 and control is returned to step S28.

If the variable i is equal to or larger than 5 in step S27, it is determined whether or not dd equals 0 in step S32. If dd equals 0, then 0 is substituted for dw in step S33, Unless dd is zero, the value of nn. $smf_{13}$K·ej·dw/dd is substituted for dw in step S34.

Next, 0 is substituted for the variable j in step S35, and nn. xp is substituted for the variable j in step S36. Then, it is determined in step S37 whether or not the difference obtained by subtracting 1 from the variable j is smaller than 0. If the difference is smaller than 0, then 7 is substituted for the variable j in step S38.

Then, 0 is substituted for the variable i in step S39, and it is determined in step S40 whether or not the variable i is 400. Unless the variable i is 400, the value obtained by performing a double-precision operation on smf[j][i]/255+dw is substituted for dd in step S41. If dd is larger than 1 (step S42), 1 is substituted for dd in step S44. If dd is equal to or smaller than 0 (step S43), then 0 is substituted for dd in step S45.

Smf[j][i] can be 255 at maximum, and is the j(j=0~400)th value of the i(i=0~7)th sampling membership function.

Next, an unsigned integer of dd*255 is substituted for smf[j][i] in step S46, and control is returned to step S40.

When the variable i becomes 400 after 400 times repeating the operations in steps S40 through S46, it is determined in step S47 whether or not variable j is 8. Unless the variable j is 8, control is returned to step S36 and the process terminates when the variable j becomes 8.

Figure 8:
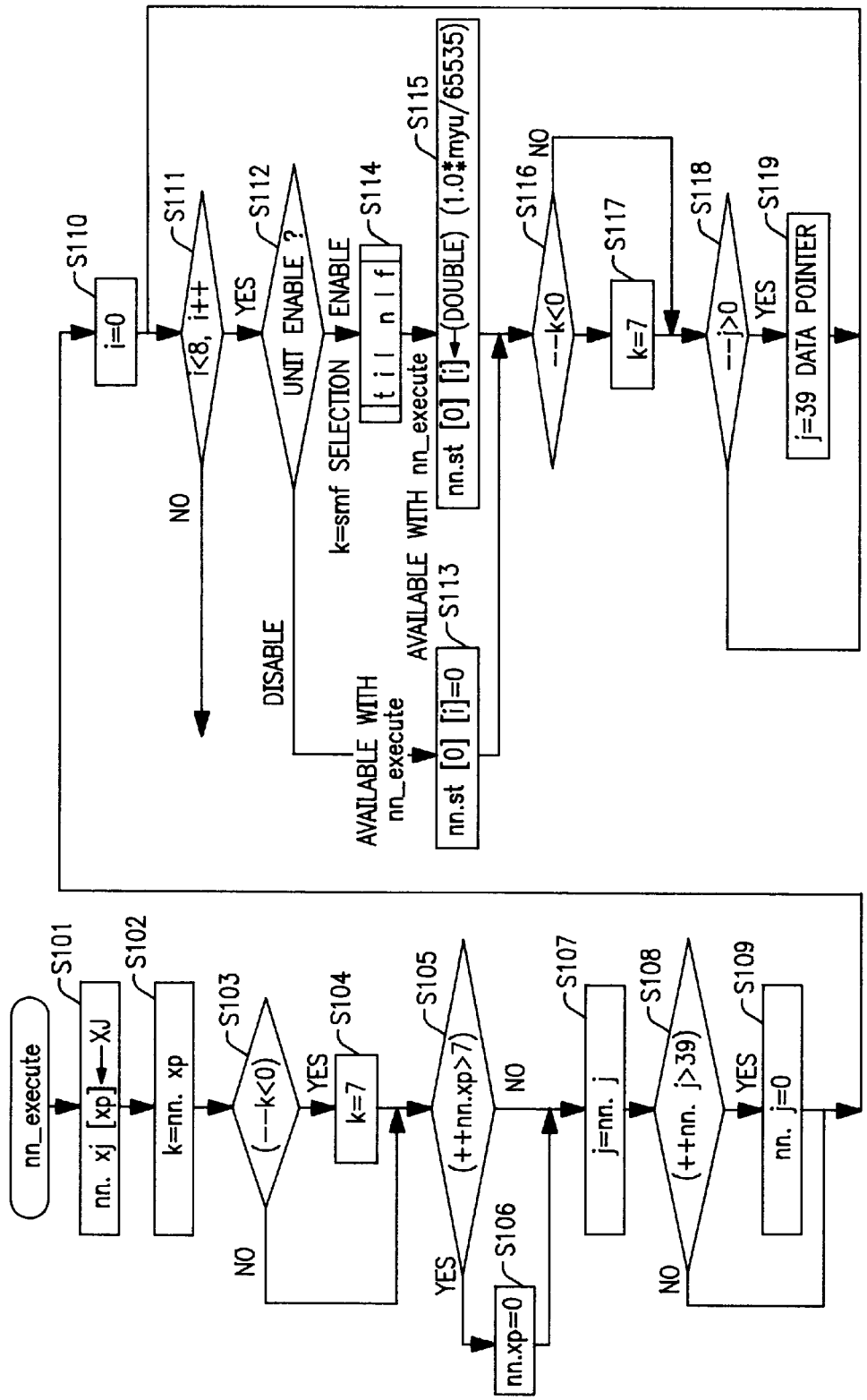
FIG. 8 is a flowchart (1) showing the operations of the active noise control apparatus according to an embodiment of the present invention.
Figure 9:
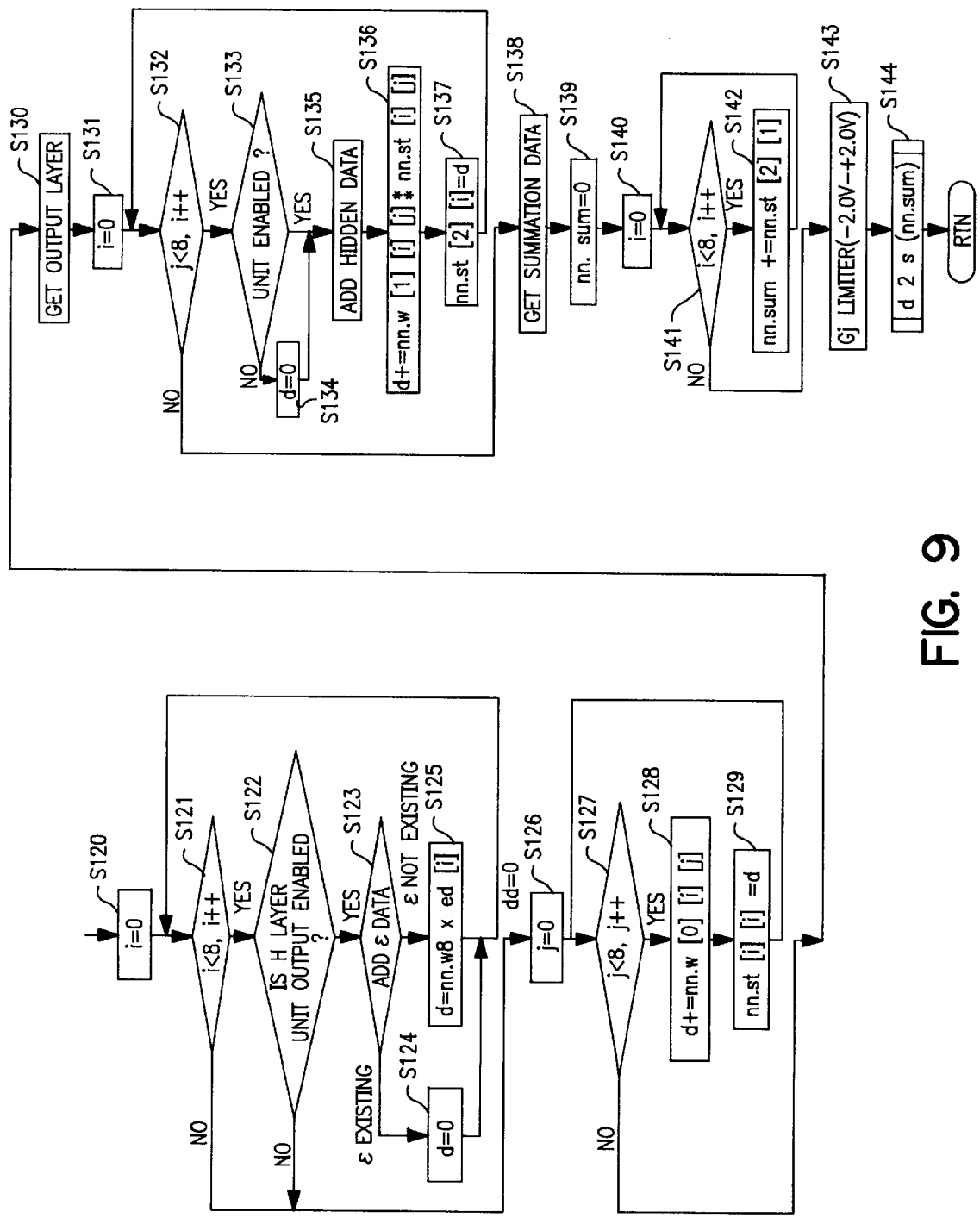
FIG. 9 is a flowchart (2) showing the operations of the active noise control apparatus according to an embodiment of the present invention.

FIGS. 8 and 9 are flowcharts showing the operations of the active noise control apparatus according to the first embodiment of the present invention. The flowcharts are prepared in the C language. A sampling membership function is performed in steps S110 through S119 shown in FIG. 8. A net ε is added in steps S120 through S125 shown in FIG. 9. The layer O is processed in steps S126 through S130 shown in FIG. 9. The layer H is processed in steps S131 through S137 shown in FIG. 9.

In FIG. 8, A value of XJ is substituted for nn. xj[xp] in step S101, and a value of nn.xp is substituted for the variable k in step S102. It is determined in step S103 whether or not the value obtained by subtracting 1 from the variable k is smaller than 0. If it is smaller than 0, then 7 is substituted for the variable k in step S104.

Then, it is determined in step S105 whether or not the value obtained by adding 1 to a value of nn. xp is larger than 7. If it is larger than 7, 0 is substituted for nn. xp in step S106.

A value of nn. j is substituted for the variable j in step S107. It is determined in step S108 whether or not the value obtained by adding 1 to the value of nn. j is larger than 39. If it is larger than 39, then 0 is substituted for nn. j in step S109.

Next, 0 is substituted for the variable i in step S110, and it is determined in step S111 whether or not the variable i is smaller than 8. If the variable i is smaller than 8, then the operations in steps S112 through S119 are performed and 1 is added to the variable i. When the variable i becomes 8 or larger than 8, control is passed to step S120 shown in FIG. 9.

The 'unit enabled' determination is made in step S112. If it is determined that the unit is disabled, 0 is substituted for nn. st[0][i] in step S113. If it is determined that the unit is enabled, a function is processed using tilnlf in step S114, and a double-precision value of 0*myu/65535 is substituted for nn. st[0][i] in step S115.

An argument of the function obtained using tiln1f in step S114 is (nn. xj[k]. j/5. &myu). The value of Xj represented by the value of the pointer k is obtained, and the paging result of 8 sampling membership functions is represented by the value obtained by dividing the current j (j=0~39) by 5 and stored at the address indicated by myu.

Then, it is determined in step S116 whether or not the value obtained by subtracting 1 from the variable k is smaller than 0. If it is smaller than 0, then 7 is substituted for the variable k in step S117.

Next, it is determined in step S118 whether or not the value obtained by subtracting 1 from the variable j is smaller than 0. If it is smaller than 0, 39 is substituted for the variable j in step S119.

In FIG. 9, 0 is substituted for the variable i in step S120, and it is determined in step S121 whether or not the variable i is smaller than 8. When the variable 8 is smaller than 8, 1 is added to the variable i by performing the processes in steps S122 through S125. When the variable i is equal to or larger than 8, then control is passed to step S126.

The output enable determination is made for the unit in the layer H in step S122. If the determination result does not indicate "enabled", control is passed to step S126. If it indicates "enabled", then it is determined in step S123 whether or not a net $\epsilon$ exists. If yes, then 0 is substituted for d in step S124. If the net $\epsilon$ does not exist, then nn. w8 x ed[i] is substituted for d in step S125, and control is returned to step S121.

Then, 0 is substituted for the variable j in step S126, and it is determined in step S127 whether or not the variable j is smaller than 8. When the variable j is smaller than 8, the processes in steps S128 and S129 are performed and 1 is added to the variable j. When the variable j is equal to or larger than 8, the output layer is acquired in step S130.

In step S128, a sum of d and nn. w[0][i][j] is substituted for d, d is substituted for nn. st[1][I] in step S129, and control is returned to step S127.

Next, 0 is substituted for the variable i in step S131, and it is determined in step S132 whether or not the variable i is smaller than 8. If the variable i is smaller than 8, then 1 is added to the variable i after performing the processes in steps S133 through S137. When the variable i is equal to or larger than 8, the summation data is acquired in step S138.

The "unit enabled" determination is made in step S133. If it is not enabled, then 0 is substituted for d in step S134.

Next, the hidden data is added in step S135. A sum of d and nn. w[1][i][j]*nn. st[i][j] is substituted for d in step S136, and d is substituted for nn. st[2][i] in step S137, thereby returning control to step S132.

Then, 0 is substituted for nn. sum in step S139, and 0 is substituted for the variable i in step S140. It is determined in step S141 whether or not the variable i is smaller than 8. If it is smaller than 8, then a sum of nn. sum and nn. st[2][i] is substituted for nn. sum in step S142, and 1 is added to the variable i. When the variable i is equal to or larger than 8, the limiter of Gi is processed between -2V through +2V in step S143 and the value of double of nn. sum is converted into a signed integer in step S144, thereby terminating the process.

The first embodiment of the present invention has been described above. However, the present invention is not limited to the above described embodiment, and there can be various embodiments.

For example, the nonlinear functions 10 through 17 and 56 through 63 shown in FIG. 2 can be incorporated into the input layer I in the neural networks 92 and 93, or into the hidden layer H or output layer O in the neural networks 92 and 93.

According to the above described embodiment, the weight of the output layer O in the neural networks 92 and 93 is output by the update units 44 and 47. The weight of the hidden layer H or the weights of both hidden layer H and output layer O in the neural networks 92 and 93 can be updated.

According to the above described embodiment, an output signal from the output layer O in the neural network 93 is input to the hidden layer H in the neural network 92. The output signal from the output layer O in the neural network 93 can be input to the output layer O or both of the hidden layer H and output layer O in the neural network 92.

Furthermore, the hidden layer H in the neural networks 92 and 93 can be omitted, and the nonlinear functions 10 through 17 and 56 through 63 can be realized in the neural network.

Noises can be cancelled by generating a cancelling sound, or can be converted into acceptable sounds.

According to the first embodiment of the present invention, as described above, a cancelling sound can be generated without a digital filter, thereby reducing the circuit scale of the active noise control apparatus.

The active noise control apparatus according to the second embodiment of the present invention is described below by referring to the attached drawings. The active noise control apparatus according to the second embodiment is designed such that the active noise control apparatus according to the first can be applicable to a 3-dimensional sound field.

Figure 13:
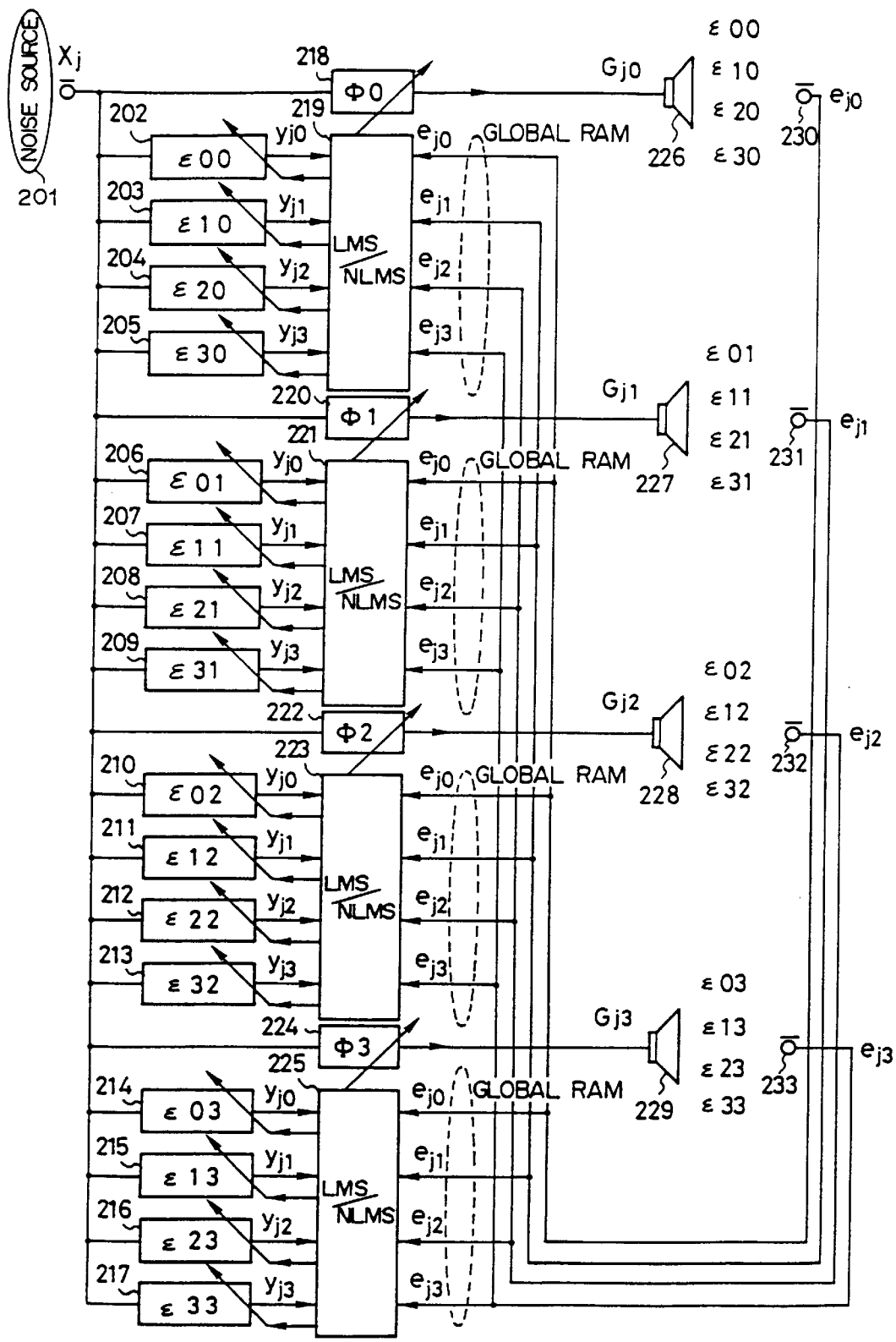
FIG. 13 is a block diagram showing the configuration of the active noise control apparatus according to the second embodiment of the present invention.

FIG. 13 is a block diagram showing the configuration of the active noise control apparatus according to the second embodiment of the present invention.

In FIG. 13, 201 is a noise source. 202 through 217 are error path units. 218, 220, 222, and 224 are noise control units. 219, 221, 223, and 225 are update units. 226 through 229 are speakers. 230 through 233 are microphones.

Each of the error path units 202 through 217 is formed using a neural network as in the acoustic coupling error processing unit 48 shown in FIG. 2. Each of the noise control units 218, 220, 222, and 224 is formed using a neural network as in the noise control unit 2 shown in FIG. 2. Each of the update units 219, 221, 223, and 225 is similarly formed as in the update units 44 through 47 shown in FIG. 2.

$\epsilon 00$ is an acoustic coupling path between the speaker 226 and the microphone 230. $\epsilon 10$ is an acoustic coupling path between the speaker 226 and the microphone 231. $\epsilon 20$ is an acoustic coupling path between the speaker 226 and the microphone 232. $\epsilon 30$ is an acoustic coupling path between the speaker 226 and the microphone 233.

$\epsilon 01$ is an acoustic coupling path between the speaker 227 and the microphone 230. $\epsilon 11$ is an acoustic coupling path between the speaker 227 and the microphone 231. $\epsilon 21$ is an acoustic coupling path between the speaker 227 and the microphone 232. $\epsilon 31$ is an acoustic coupling path between the speaker 227 and the microphone 233.

ε02 is an acoustic coupling path between the speaker 228 and the microphone 230. ε12 is an acoustic coupling path between the speaker 228 and the microphone 231. ε22 is an acoustic coupling path between the speaker 228 and the microphone 232. ε32 is an acoustic coupling path between the speaker 228 and the microphone 233.

ε03 is an acoustic coupling path between the speaker 229 and the microphone 230. ε13 is an acoustic coupling path between the speaker 229 and the microphone 231. ε23 is an acoustic coupling path between the speaker 229 and the microphone 232. ε33 is an acoustic coupling path between the speaker 229 and the microphone 233.

The error path unit 202 stores the result of learning the acoustic coupling path ε00 as the weight of the neural network. The error path unit 203 stores the result of learning the acoustic coupling path ε10 as the weight of the neural network. The error path unit 204 stores the result of learning the acoustic coupling path ε20 as the weight of the neural network. The error path unit 205 stores the result of learning the acoustic coupling path ε30 as the weight of the neural network.

The error path unit 206 stores the result of learning the acoustic coupling path ε01 as the weight of the neural network. The error path unit 207 stores the result of learning the acoustic coupling path ε11 as the weight of the neural network. The error path unit 208 stores the result of learning the acoustic coupling path ε21 as the weight of the neural network. The error path unit 209 stores the result of learning the acoustic coupling path ε31 as the weight of the neural network.

The error path unit 210 stores the result of learning the acoustic coupling path ε02 as the weight of the neural network. The error path unit 211 stores the result of learning the acoustic coupling path ε12 as the weight of the neural network. The error path unit 212 stores the result of learning the acoustic coupling path ε22 as the weight of the neural network. The error path unit 213 stores the result of learning the acoustic coupling path ε32 as the weight of the neural network.

The error path unit 214 stores the result of learning the acoustic coupling path ε03 as the weight of the neural network. The error path unit 215 stores the result of learning the acoustic coupling path ε13 as the weight of the neural network. The error path unit 216 stores the result of learning the acoustic coupling path ε23 as the weight of the neural network. The error path unit 217 stores the result of learning the acoustic coupling path ε33 as the weight of the neural network.

Described below are the operations of the active noise control apparatus according to the second embodiment of the present invention.

In FIG. 13, the input signal Xj from the noise source 201 is provided for the noise control units 218, 220, 222, and 224. A weight operation and function process is performed on the current and past input signal Xj. Output signals from the noise control units 218, 220, 222, and 224 are respectively provided for the speakers 226 through 229 and output as cancelling sounds.

The cancelling sounds output from the speakers 226 through 229 are respectively detected by the microphones 230 through 233 together with primary noises. The error signals $e_{j0}$ through $e_{j3}$ from the microphones 230 through 233 are respectively provided for the update units 219, 221, 223, and 225.

The input signal Xj from the noise source 201 is provided for the error path units 202 through 217. A weight operation and function process is performed on the current and past input signal Xj. The output signals $y_{j0}$ through $y_{j3}$ from the error path units 202 through 205 are output to the hidden layer H or output layer O in the neural network of the noise control unit 218. The output signals $y_{j0}$ through $y_{j3}$ from the error path units 206 through 209 are output to the hidden layer H or output layer O in the neural network of the noise control unit 220. The output signals $y_{j0}$ through $y_{j3}$ from the error path units 210 through 213 are output to the hidden layer H or output layer O in the neural network of the noise control unit 222. The output signals $y_{j0}$ through $y_{j3}$ from the error path units 214 through 217 are output to the hidden layer H or output layer O in the neural network of the noise control unit 224.

The update unit 219 updates the nonlinear function and weight of the hidden layer H or output layer O in the neural network of the noise control unit 218 according to the error signals $e_{j0}$ through $e_{j3}$, and updates the nonlinear function and weight of the hidden layer H or output layer O in the neural network of the error path units 202 through 205.

The update unit 221 updates the nonlinear function and weight of the hidden layer H or output layer O in the neural network of the noise control unit 221 according to the error signals $e_{j0}$ through $e_{j3}$, and updates the nonlinear function and weight of the hidden layer H or output layer O in the neural network of the error path units 206 through 209.

The update unit 223 updates the nonlinear function and weight of the hidden layer H or output layer O in the neural network of the noise control unit 222 according to the error signals $e_{j0}$ through $e_{j3}$, and updates the nonlinear function and weight of the hidden layer H or output layer O in the neural network of the error path units 210 through 213.

The update unit 225 updates the nonlinear function and weight of the hidden layer H or output layer O in the neural network of the noise control unit 224 according to the error signals $e_{j0}$ through $e_{j3}$, and updates the nonlinear function and weight of the hidden layer H or output layer O in the neural network of the error path units 214 through 217.

For example, the weight change dw made by the update units 219, 221, 223, and 225 is calculated by the following equation.

$$dw = fj(e_{j0} + e_{j1} + e_{j2} + e_{j3})$$

Described below is the learning method of the active noise control apparatus according to an embodiment of the present invention. The active noise control apparatus comprises, in addition to the active noise control path (ANCP), an active feedback control path (AFCP), and a residual error control path (RECP). When the active noise control apparatus shown in FIG. 2 learns the active feedback control path, it comprises a third neural network in addition to the neural networks 92 and 93.

For example, a real-time learning is performed on the active noise control path, the active feedback control path, and residual error control path, and a preliminary learning is performed on the active feedback control path and the residual error control path.

Described below is the learning method of the residual error control path.

Figure 14:
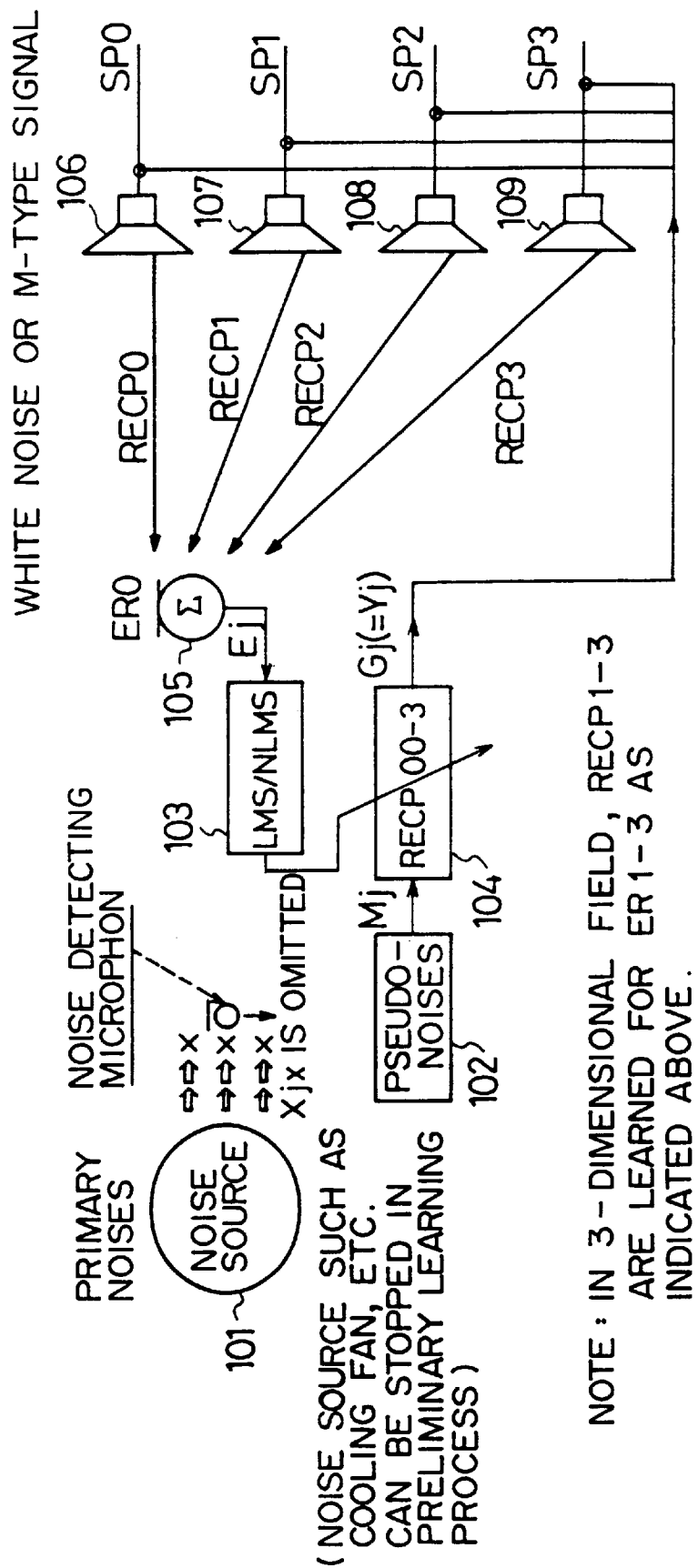
FIG. 14 shows the learning method of the residual error control path according to an embodiment of the present invention.

In FIG. 14, 101 is a noise source such as a cooling fan, 102 is a pseudo-noise such as white noise and an M-type signal, 103 is an update unit using the least mean square method or normalized least mean square method, 104 is a residual error control system, 105 is an acoustic coupling system, and 106 through 109 are speakers.

The pseudo-noise Mj is provided for the residual error control system 104, and a signal Gj from the residual error control system 104 is provided for the speakers 106 through 109. The update unit 103, as shown in FIG. 15, learns the transmitting system of the residual error control path by updating the weight of the residual error control system 104 according to an error signal Ej from the acoustic coupling system 105.

In a preliminary learning process, the noise source 101 such as a cooling fan, etc. can be stopped.

For example, when the acoustic coupling error processing unit 48 shown in FIG. 2 learns the residual error control path, the pseudo-noise Mj is input as an input signal Xj with the weight of the neural network 92 of the noise control unit 2 set to 0. The update unit 46 updates the nonlinear functions 56 through 63. The update unit 47 updates the weight of the neural network 93 to learn the residual error control path corresponding to the error paths between the speaker 43 and the microphone 91.

As described above, according to the second embodiment of the present invention, a cancelling sound can be generated in a 3-dimensional sound field without a digital filter, thereby reducing the size of a required circuit.

Furthermore, since error information can be processed in parallel, there is no need for an error scanning algorithm for updating a filter coefficient while scanning an error sensor.

Described above is an example of a noise reducing method using an active noise control apparatus. However, the present invention is not limited to a noise attenuating system, but can be applied to various fields in industry.

For example, the present invention can be applied to an earthquake-proof and control system, and a sound processing system and an image processing system including a telephone unit.

What is claimed is:

1. An active noise control apparatus comprising:

a first neural network that performs distributed processing in parallel on current and previous time series data corresponding to primary noises to generate an output specifying a cancelling sound corresponding to a primary path for transmission of the primary noises;

error detecting means for detecting an error signal between the cancelling sound generated according to the output from said first neutral network and the transmitted primary noises;

a second neural network that receives the current and previous time series data corresponding to the primary noises, and provides an output to said first neural network for acoustic error coupling corresponding to an error path from a speaker to said error detecting means; and update means for updating weight values of nonlinear functions of said first and second neural networks according to the error signal.

2. The active noise control apparatus according to claim 1, wherein:

the cancelling sound is output from a speaker; and said error detecting means comprises an error detecting microphone.

3. The active noise control apparatus according to claim 1, wherein the output of said first neural network specifies the cancelling sound based on the primary path and the error path.

4. The active noise control apparatus according to claim 1, wherein said second neural network outputs a reference signal to a hidden layer of said first neural network.

5. The active noise control apparatus according to claim 1, wherein each of said first and second neural networks comprises nonlinear functions in an input layer, a hidden layer, or an output layer thereof.

6. The active noise control apparatus according to claim 1, wherein said update means updates a weight between an input layer and a hidden layer and a weight between the hidden layer and an output layer of a neural network selected from said first and second neural networks.

7. The active noise control apparatus according to claim 1, wherein the output signal from said second neural network is input to an input layer or an output layer of said first neural network.

8. The active noise control apparatus according to claim 1, wherein an active noise control path is learned in real time in said first neural network.

9. The active noise control apparatus according to claim 1, wherein a residual error control path is preliminarily learned in said second neural network.

10. An active noise control apparatus comprising:

N first neural networks that receive, in parallel, current and previous time-series data corresponding to primary noises;

N error detecting means for detecting an error signal between secondary noises generated by an output from said first neural network and transmitted primary noises;

$N^2$ second neural networks for learning N residual error control paths in which the secondary noises from said first neural network reach respective ones of the error detecting means, and for providing learning results to respective one of the first neural networks; and N update means for receiving error signals from respective ones of the error detecting means, and updating weights of said first and second neural networks for cancellation of the transmitted primary noises.

11. An active noise control system comprising:

a noise source that generates primary noises;

a first neural network that receives, in parallel, current and previous noise data from said noise source through a first nonlinear function;

a second neural network that receives, in parallel, the current and previous noise data from said noise source through a second nonlinear function;

acoustic means for generating secondary noises for cancelling transmitted primary noises according to an output signal from said first neural network;

detecting means for detecting an error signal between the transmitted primary noises and a cancelling noise generated from the secondary noises; and update means for updating at least one of a weight of said first neural network, a weight of said second neural network, said first nonlinear function, and said second nonlinear function according to the error signal detected by said detecting means.

12. A waveform converting apparatus, comprising:

delay means for delaying first waveform data;

a first neural network for receiving current and previous first waveform data;

a second neural network for receiving the current and previous first waveform data and providing an output to said first neural network;

adding means for adding an output result from each node in an output layer of said first neural network and outputting second waveform data;

error detecting means for detecting an error between a waveform corresponding to the first waveform data and a waveform corresponding to the second waveform data; and update means for updating at least one of a nonlinear function and a weight of each of said first and second neural networks according to the error, at least one of the nonlinear function and the weight of the one said first and second neural networks being updated for combining the waveform corresponding to the second waveform data with the waveform corresponding to the first waveform data to make a desired waveform.

13. The waveform converting apparatus according to claim 12, wherein the desired waveform corresponds to cancellation of the waveform corresponding to the first waveform data.

14. An active noise control method comprising the steps of:

processing, in parallel, current and previous time-series data corresponding to primary noises in a first neural network and a second neural network;

inputting an output from said second neural network to said first neural network;

detecting an error signal between secondary noises generated from the output of said first neural network and transmitted primary noises;

updating a weight of said first and second neural networks according to the error signal;

preliminarily learning a residual error control path by setting a weight of a first neural network to 0, and by learning a weight of the second neural network whose output is connected to a node of the first neural network; and inputting current and previous time-series data to the first and second neural networks, and updating and executing the first neural network in one sampling time of the time-series data.

15. A computer-readable storage medium encoded with a noise control program, said program comprising the functions of:

processing, in parallel, current and previous time-series data corresponding to primary noises in a first neural network and a second neural network;

inputting an output from said second neural network to said first neural network;

detecting an error signal between secondary noises generated from the output of said first neural network and transmitted primary noises;

updating a weight of said first and second neural networks according to the error signal;

preliminarily learning a residual error control path by setting a weight of a first neural network to 0, and by learning a weight of the second neural network whose output is connected to a node of the first neural network; and inputting current and previous time-series data to the first and second neural networks, and updating and executing the first neural network in one sampling time of the time-series data.

16. An active control apparatus, comprising:

a control unit including a first neural network having a weight updated at a current time step by a first update signal;

a coupling error processing unit including a second neural network having a weight updated at the current time step by a second update signal based on a detection signal indicating a state of an object system of said apparatus at a previous time step; and an additional coupling error processing unit including a third neural network having a weight updated at the current time step by a third update signal based on an additional detection signal indicating the state of the object system at the previous time step.

17. The active control apparatus according to claim 16, further comprising an update unit that generates the second update signal based on an error signal representing a difference between the state of the object system at the previous time step and a desired state.

* * * * *

UNITED STATES PATENT AND TRADEMARK OFFICE
CERTIFICATE OF CORRECTION

PATENT NO.  : 5,949,890
DATED       : September 7, 1999
INVENTOR(S) : Tadashi OHASHI It is certified that error appears in the above-identified patent and that said Letters Patent is hereby corrected as shown below:

Col. 15, line 42, change "neutral" to --neural--.

Signed and Sealed this

Twenty-fifth Day of January, 2000

Attest:

Attesting Officer

Acting Commissioner of Patents and Trademarks